United States Patent [19]
Anderson

[11] Patent Number: 5,721,783
[45] Date of Patent: Feb. 24, 1998

[54] HEARING AID WITH WIRELESS REMOTE PROCESSOR

[76] Inventor: James C. Anderson, 40 Aran Rd., Westwood, Mass. 02090

[21] Appl. No.: 479,629

[22] Filed: Jun. 7, 1995

[51] Int. Cl.$^6$ .................................................. H04R 25/00
[52] U.S. Cl. .......................... 381/68.6; 381/68; 381/68.2; 381/68.4
[58] Field of Search ............... 381/68, 68.2, 68.4, 381/68.6; 342/42–51, 2; 340/6, 825.54, 505

[56] References Cited

U.S. PATENT DOCUMENTS

| | | | |
|---|---|---|---|
| 2,774,060 | 12/1956 | Richardson | 325/9 |
| 3,384,892 | 5/1968 | Postmann | 343/6.5 |
| 3,493,955 | 2/1970 | Minasy | 340/258 |
| 3,518,546 | 6/1970 | Augenblick | 325/8 |
| 3,601,550 | 8/1971 | Spracklen | 179/82 |
| 3,711,848 | 1/1973 | Martens | 340/280 |
| 3,754,226 | 8/1973 | Fearon | 340/280 |
| 4,051,331 | 9/1977 | Strong et al. . | |
| 4,063,229 | 12/1977 | Vaughan et al. . | |
| 4,334,315 | 6/1982 | Ono et al. . | |
| 4,791,672 | 12/1988 | Nunley et al. . | |
| 4,918,736 | 4/1990 | Bordewijk | 381/68 |
| 4,918,737 | 4/1990 | Luethi . | |
| 4,947,432 | 8/1990 | Topholm . | |
| 5,027,410 | 6/1991 | Williamson et al. . | |
| 5,115,160 | 5/1992 | Knoll et al. | 310/313 R |
| 5,202,927 | 4/1993 | Topholm | 381/68.6 |
| 5,210,803 | 5/1993 | Martin et al. . | |
| 5,226,086 | 7/1993 | Platt | 381/58 |
| 5,241,923 | 9/1993 | Janning | 340/573 |
| 5,295,191 | 3/1994 | Van Vroenhoven . | |
| 5,303,306 | 4/1994 | Brillhart et al. | 381/68.2 |
| 5,390,254 | 2/1995 | Adelman . | |
| 5,479,522 | 12/1995 | Lindemann et al. | 381/68.2 |
| 5,613,495 | 3/1997 | Mills et al. | 128/696 |
| 5,636,285 | 6/1997 | Sauer | 381/68.2 |

FOREIGN PATENT DOCUMENTS 2651634  3/1991  France .

OTHER PUBLICATIONS

"Q & A about Biological Effects and Potential Hazards of RF Radiation", OET Bulletin 56, FCC, Washington, D.C., Jan. 1989, pp. 1–3.

"How to Buy a Hearing Aid", Consumer Reports Magazine, Nov. 1992, pp. 716–712.

T. Tanji, "A digital Radio Hearing Aid", I-P-14, Program and Abstracts of First Biennial Conference on Advancing Human Communication: An Interdisciplinary Forum on Hearing Aid Research and Development, National Institutes of Health, Bethesda, MD, Sep. 11–13, 1995.

SHS Wireless Radio Communications Data Sheet From E.A.R. Inc.; Jan. 1990.

CROS Product Data Sheets From Telex Communications, Inc.; Jan. 1989.

H. Levitt, A. Neuman, R. Mills and T. Schwander, "Digital Master Hearing Aid" Journal of Rehabilitation Research and Development, vol. 23, No. 1, 1986, pp. 79–87, May 1986.

*Primary Examiner*—Curtis Kuntz
*Assistant Examiner*—Rexford N. Barnie
*Attorney, Agent, or Firm*—Richard F. Benway; Martin M. Santa

[57] ABSTRACT

A hearing aid or audio communication system includes an earpiece (10) that can be hidden in the ear canal, and which communicates wirelessly with a remote processor unit, or RPU (16), that enhances audio signals and can be concealed under clothing. Sounds from the environment are picked up by a microphone (12) in the earpiece and sent with other information over a two-way wireless link (17) to the RPU (16). The wireless link (17) uses microwaves for component miniaturization. Furthermore, use of radar technology to implement the wireless link (17), with an RPU (16) interrogator and earpiece (10) transponder, reduces earpiece size and power, as no microwave oscillator is needed in the earpiece (10). Optional secondary wireless link circuitry (19) can be used between the RPU (16) and a cellular telephone system or other sources of information. Electronic voice recognition and response can control system operation.

71 Claims, 9 Drawing Sheets

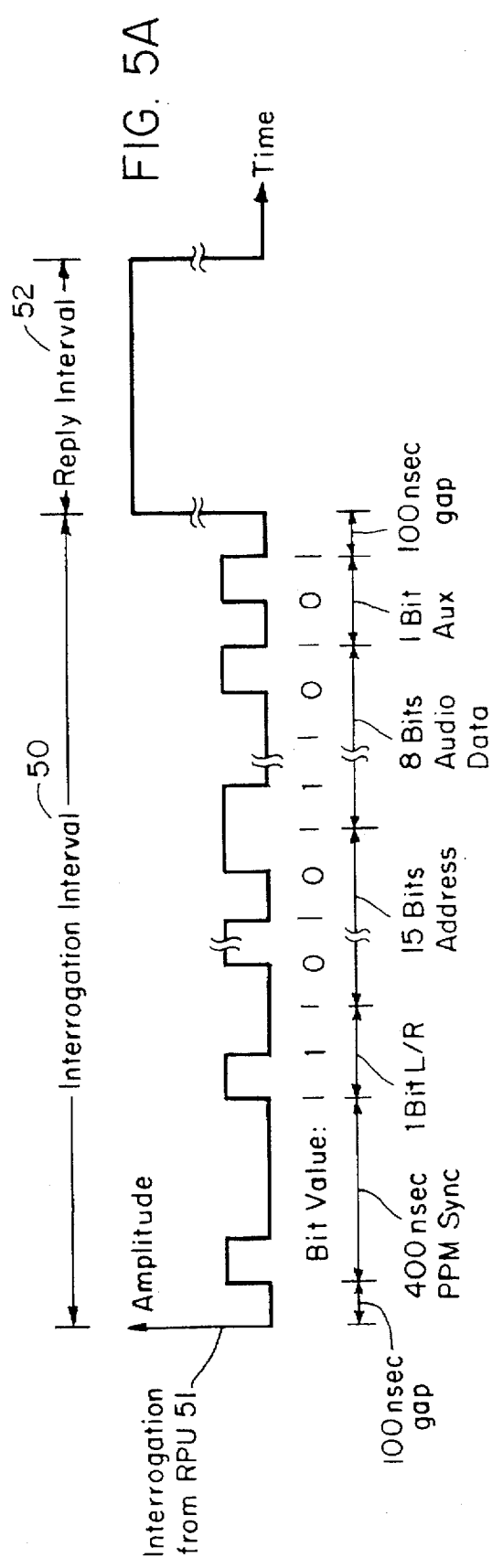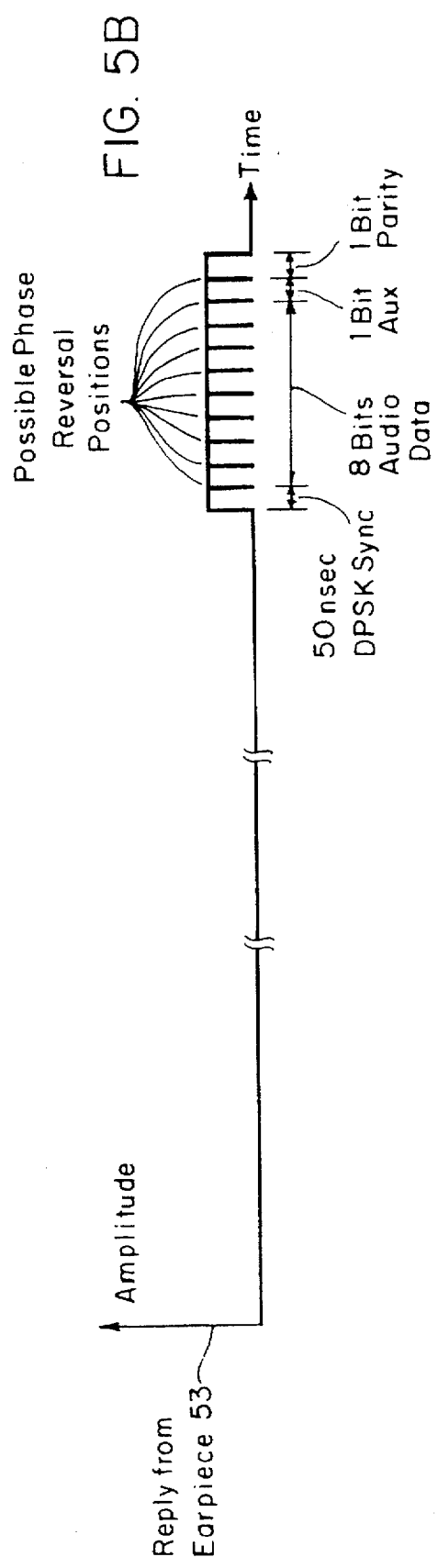

HEARING AID WITH WIRELESS REMOTE PROCESSOR

BACKGROUND OF THE INVENTION

1. Field of the Invention

The present invention is directed to hearing aids, and in particular to a hearing aid having an earpiece housing worn in or at the ear and a remote processor unit (RPU) worn by or located near the user that wirelessly receives signals from and transmits signals to the earpiece. The present invention is also directed to the use of hearing aid systems as wireless communication devices for hands-free cellular telephone and mobile radio communication "handsets," covert operation and control of hearing aids, hearing protection and noise cancellation simultaneous with binaural hearing aid functions, hearing test equipment, location of misplaced hearing aid system components and wireless cochlear implants.

2. Brief Description of the Related Art

In the prior art, a basic hearing aid without remote control is a self-contained earpiece comprising a microphone, speaker and associated processor electronics. In such hearing aids, the earpiece microphone converts acoustic waves into electrical representations of the acoustic waves, the electrical signals are amplified by the earpiece processor electronics and converted back into acoustic waves by the earpiece speaker. A remote control (see, e.g., U.S. Pat. No. 4,918,736) that controls earpiece amplification functions (e.g., volume) via a one-way wireless link from the remote control to the earpiece is sometimes used in the prior art, but the path taken by the electrical signals that represent the acoustic waves (known in the art as the "audio path") is the same whether or not a remote control is used; i.e., the audio path is from the microphone to the speaker via the earpiece electronics.

Wireless hearing aids using a one-way radio frequency (RF) transmission path, comprising a wireless microphone transmitter (not normally worn at the ear) and a wireless receiver (normally worn at the ear) are well known in the prior art. Such devices commonly use the "auditory assistance device" RF bands near 73 MHz (see the U.S. Code of Federal Regulations, 47 CFR Ch. 1, Para. 15.237) and have proven effective as teaching aids for hearing-impaired students in a classroom setting. Thus, in the prior art, RF transmissions are sent from a hand-held wireless microphone (not a microphone located in an earpiece) to a wireless receiver in or near an earpiece, providing a one-way radio transmitter and receiver system for the audio path.

The present invention uses an audio path that is different from the audio path used by devices in the prior art. The present invention uses a primary two-way wireless link (not a one-way link as in the prior art) between an earpiece worn in or at the user's ear and an RPU worn by or located near the user. In the present invention, audio signals from the environment are picked up by a microphone in the earpiece (not a hand-held microphone as used by wireless hearing aids in the prior art) and transmitted over the primary two-way wireless link to the RPU (instead of going to processor electronics contained in the earpiece, as in basic hearing aids known in the prior art), where the audio signals are enhanced according to the user's needs before transmission over the primary wireless link to the earpiece. Signal processing is performed in the RPU rather than the earpiece to take advantage of relaxed size and power constraints. This new approach eliminates the need for most physically large and power-consuming electronics in the earpiece, eliminates the need for conventional remote controls, and provides a variety of optional features (e.g., telephone communication capability via a secondary two-way wireless link) not available in the prior art. Note that the present invention also maintains all capabilities (e.g., acoustic feedback reduction and adaptive volume control) of prior art devices.

Although cordless and cellular telephone handsets (as well as wireless communication headsets) well known in the art contain a microphone, radio transceiver (transmitter and receiver) and speaker, such devices are not used for the reception, enhancement and subsequent reproduction of audio signals from the ambient environment as required for a hearing aid application. Such devices do not act as hearing aids because they do not provide the user with enhanced sounds from the user's immediate surroundings, but only provide sounds from another user.

SUMMARY OF THE INVENTION

It is an object of the present invention to provide a new and useful auditory aid for hearing-impaired persons (i.e., those having certain residual hearing) by removing audio signal enhancement functions from the earpiece and placing them in an RPU. Use of an RPU provides several advantages over systems that attempt to place all system capabilities within the earpiece. The RPU approach allows a simple earpiece design comprising a miniature low-power wireless transceiver, microphone and speaker. Note that the speaker is also known in the hearing aid art as a "receiver," but the term "speaker" is used here to avoid confusion (similarly, the term "talker," not "speaker," is used to describe a human producing vocal sounds). The resulting earpiece is extremely small, can be hidden from view in the ear canal if desired, and allows complete freedom of movement when a primary two-way wireless link to the RPU is used. Processing for all major system capabilities, such as amplification and other forms of signal enhancement, takes place in the RPU where size and power constraints are relaxed, leading to a cost-effective design.

Another object of this invention is to provide supplemental audio information (e.g. a verbal warning from the RPU that an earpiece battery is low) and communication services (e.g., cellular telephone and paging services) to the user via the hearing aid system. Such services are accessed in a manner that can be made imperceptible to a casual observer if desired. The RPU (which contains a digital signal processor or other computer) acts as one source of information, e.g., by using a synthesized voice message to provide the time of day, and the RPU can also be used to access a secondary wireless link to the general subscriber telephone network or voice paging services. User control of hearing aid parameters and requests for information are accomplished using pushbuttons located on the RPU (including pushbuttons suitable for data entry in a covert manner) or voice recognition. Many sensors and peripheral devices can reside in or be attached to the RPU by wired or wireless means, and can provide a variety of information for different applications (e.g., heart pulse rate) as audio in the user's earpiece.

A further object of this invention is to provide some degree of protection for the residual hearing capability of a hearing-impaired user (or a non-impaired user who wishes to avoid impairment) in a wireless hearing aid system having the simultaneous capabilities of noise cancellation and binaural processing (e.g., directionality). Other objects of the invention are to provide a convenient means for testing a user's hearing capability without the need for additional equipment, to assist users in the location of misplaced hearing aid system components, and to provide profoundly deaf cochlear implant patients with a wireless system allowing improved freedom of movement compared to existing wire-connected systems.

DESCRIPTION OF THE DRAWINGS

These and other objects, features and advantages of the invention will best be understood with the aid of the following detailed description in conjunction with the accompanying drawings in which:

FIG. 5 is a waveform timing diagram showing characteristics of a typical interrogation from an RPU interrogator followed by a corresponding typical reply from an earpiece transponder.

DESCRIPTION OF THE PREFERRED EMBODIMENTS

Figure 1:
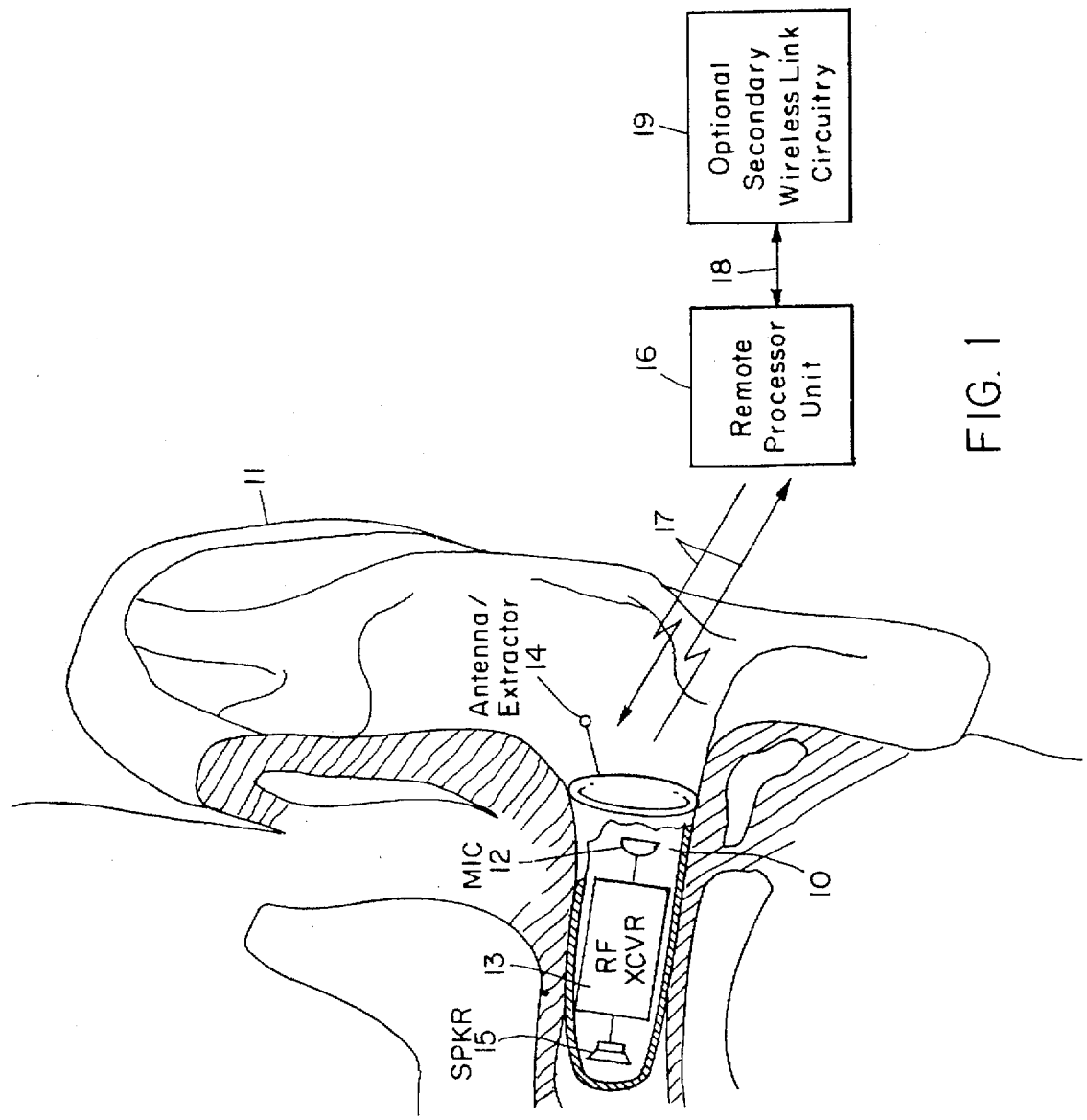
FIG. 1 is a block diagram system overview illustrating how an earpiece (comprising a microphone, RF transceiver, dual-use antenna/extractor and speaker) is worn in the ear, communicates via a primary two-way RF link with an RPU, and also communicates via an optional secondary wireless link to a telephone system.

One preferred embodiment of the invention herein described is shown in block diagram form in FIG. 1. In this figure, the earpiece 10 shown worn in the ear 11 uses a standard completely-in-the-canal (CIC) housing, well known in the art, although many other earpiece housing types known in the art (e.g., behind-the-ear, or BTE) can be used. The earpiece shown in FIG. 1 comprises a microphone 12, RF transceiver 13 with an antenna that doubles as an earpiece extractor 14, and speaker 15. Although the dual-use antenna/extractor arrangement shown in FIG. 1 is often desirable, a separate antenna or antennae can be used in conjunction with many different types of earpiece extractors as appropriate for a particular application. Antennae and extractors can be disguised as ear hair or jewelry (e.g., earrings), or conductive filaments can be permanently implanted in the ear cartilage to act as antennae using a process similar to ear piercing. The earpiece 10 communicates with a remote processor unit (RPU) 16 via a primary two-way RF link 17, although many other wireless link media (e.g., ultrasonic or infrared) may be used instead. The RPU is typically worn under clothing (e.g., carried in a pocket or purse), but may also be worn in plain sight (e.g., on a belt) if desired. The RPU 16 may be connected (via wired or wireless means 18) to optional secondary wireless link circuitry 19 that allows wireless communication between the RPU and other sources of information (e.g., the general subscriber telephone network) via a secondary wireless link. Note that the optional secondary wireless link circuitry 19 may or may not be contained within the RPU case 70 of FIG. 7.

It will be apparent to those skilled in the art that many variations of the system shown in FIG. 1 are possible, and two embodiments of the invention are described here in detail. The first preferred embodiment is a limited-feature embodiment, assembled using commercial off-the-shelf system elements, that demonstrates the basic features of a hearing aid with wireless remote processor as well as communication capability via a secondary wireless link. The second preferred embodiment is a considerably more complex full-featured embodiment for general application.

1. Limited-feature embodiment

Figure 2:
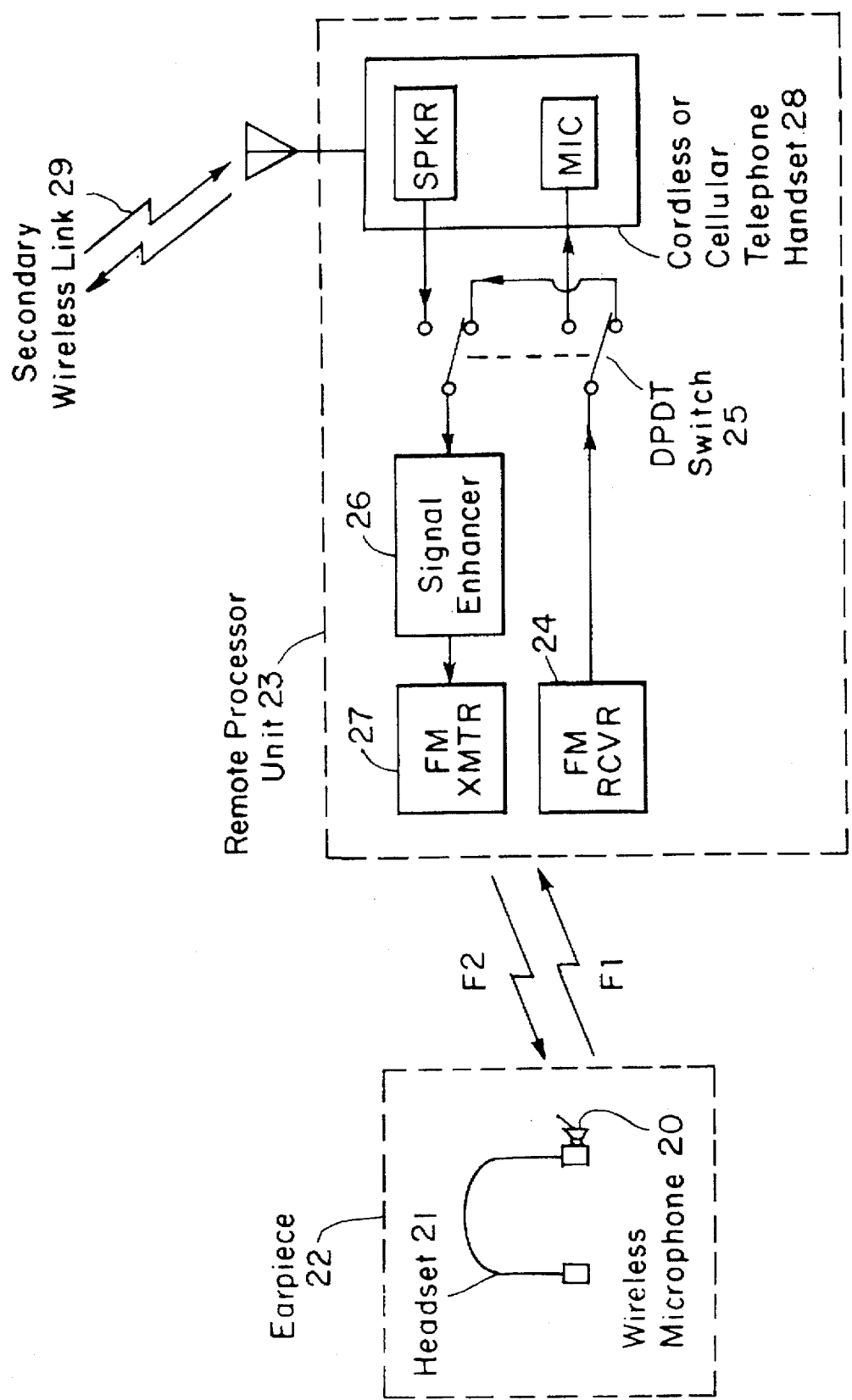
FIG. 2 is a block diagram illustrating a limited-feature preferred embodiment of the invention that uses commercial off-the-shelf system elements.

The limited-feature hearing aid embodiment shown in FIG. 2 can be fabricated using low-cost commercial off-the-shelf RF system elements operating in the standard 88 MHz to 108 MHz FM (frequency modulation) broadcast band. Although the system described here is monaural, it will be clear to those skilled in the art that a binaural (stereo) system can be constructed based on the same principles as the monaural system. Note that the earpiece 22 of FIG. 2 is physically different from the earpiece 10 of FIG. 1, but the two earpieces are functionally similar. An FM wireless microphone 20 transmitter, e.g. Radio Shack (R) model 33-1076, is mounted on an FM headset 21 receiver, e.g. Radio Shack (R) model 12-103, to form an earpiece 22 which is not necessarily hidden from view. The earpiece wireless microphone 20 transmitter is tuned to a fixed frequency F1 free of local interference, e.g. F1=106 MHz, while the earpiece headset 21 receiver is tuned to a different frequency F2 free of local interference, e.g., F2=90 MHz. The RPU 23 includes an FM receiver 24, e.g. Radio Shack (R) model 12-210, tuned to the earpiece wireless microphone 20 transmitter frequency F1 (106 MHz in this example) and operating in monaural mode (see instructions for the Radio Shack (R) model 12-210 FM receiver regarding details of operation). The FM receiver 24 speakers are removed, and a wire is installed in place of one of the speakers to connect the FM receiver 24 output to the double-pole double-throw (DPDT) switch 25 as shown in FIG. 2. When the DPDT switch 25 is in the lower position as shown in FIG. 2, a direct connection is provided between the output of the FM receiver 24 and the input of a signal enhancer 26 signal processing device. The signal enhancer 26 may be, for example, an OKI Semiconductor MSM6322 "pitch control LSI for the speech signal" which has been conveniently packaged for battery-powered operation as in the Questech International Inc. Transition 2001 telephone voice changing accessory (see the instruction sheets for these devices regarding details of operation). The output of the signal enhancer 26 is connected to the input of the RPU FM transmitter 27, which is tuned to the earpiece headset 21 receiver frequency F2 (90 MHz in this example). The RPU FM transmitter 27 may be a wireless microphone of the same type used in the earpiece, but which has been modified by disconnecting the microphone transducer and connecting the signal enhancer 26 in its place.

During normal operation, speech signals from a nearby talker (and other signals in the ambient audio environment) are picked up by the earpiece wireless microphone 20 and transmitted to the RPU FM receiver 24. The RPU FM receiver 24 output level may be adjusted using the RPU FM receiver 24 volume control. The resulting electrical waveform representing signals from the nearby talker travels through the DPDT switch 25, which is set to the lower position as shown in FIG. 2, to the signal enhancer 26. The signal enhancer 26 may be, for example, a voice changer device that varies the pitch of a received speech signal according to the setting of pushbutton controls located on the RPU signal enhancer 26. The speech signal's pitch can then be raised or lowered as desired to help compensate for a user's hearing loss relative to a particular talker's voice characteristics. The modified speech signal travels from the RPU signal enhancer 26 to the RPU FM transmitter 27, and finally to the earpiece headset 21 receiver where the signal is converted to acoustic waves heard by the user.

No user adjustments need to be made to the earpiece 22 components, and all necessary user adjustments are made using controls located at the RPU 23 (e.g., the volume is adjusted for a comfortable listening level using the RPU FM receiver 24 volume control, not the earpiece headset 21 volume control). Since no earpiece 22 user adjustments are required, the commercial wireless microphone 20 transmitter and headset 21 receiver designs used for the earpiece 22 can be modified by eliminating the unnecessary earpiece adjustment controls to achieve significant size reduction. Such miniaturization techniques are well known in the art, and schematics are available from Radio Shack (R) for the designs used in this example (see service manuals for the Radio Shack (R) model 33-1076 wireless microphone and model 12-103 headset). A set of fixed-value components can be used to replace the bulky variable components in the earpiece 22 (e.g., the volume control on the earpiece headset 21 and frequency controls on both the earpiece headset 21 and earpiece wireless microphone 20). Any resulting frequency drift effects in earpiece 22 components can be minimized by placing temperature-sensitive devices in a position where their temperature is regulated by that of the human body, which is a relatively constant 37 C (98.6 F). Such components can be bonded to the earpiece headset 21 speaker to provide the required thermal mass. A miniature speaker of the type commonly used in hearing aids can be used in place of the speaker commercially supplied with the earpiece headset 21, and a miniature microphone of the type commonly used in hearing aids can be used in place of the microphone transducer commercially supplied with the earpiece wireless microphone 20. Both the earpiece headset 21 and earpiece wireless microphone 20 can operate from the same 1.5V battery, and the entire earpiece 22 can be packaged in a standard BTE hearing aid housing if desired. Such miniaturization provides an earpiece which can be hidden from the view of a casual observer in many cases (e.g. if the user has long hair), especially when miniature ferrite antennae are used. The RPU 23 may be hidden from view when carried and operated in a pocket or purse.

The RPU 23 shown in FIG. 2 also includes, as an optional feature, a telephone handset 28 which may be a cordless handset (e.g. Panasonic model KX-T3710H), cellular handset (e.g., NEC model P120), or a cordless or cellular handset with voice-dialing capability, or any of a variety of other devices (e.g. a "walkie-talkie") capable of communication via any type of secondary wireless link 29 (e.g., RF or infrared). In this application, the handset 28 is not held in the user's hand, but instead forms a part of the RPU 23 carried on or located near the user's body. The handset 28 pushbuttons and other handset 28 controls are available at the surface of the RPU 23, and operated in the usual fashion. When communication via the secondary wireless link 29 is desired, the DPDT switch 25 is placed in the upper position (i.e., the alternate position from that shown in FIG. 2). The user's voice (and other signals in the ambient audio environment) is picked up by the earpiece wireless microphone 20, transmitted to the RPU 23 FM receiver 24, sent through the DPDT switch 25 to the microphone input of the handset 28 (the handset's microphone transducer may be removed) and transmitted on the secondary wireless link 29 to, e.g., the general subscriber telephone network. Signals from the secondary wireless link 29 are received by the handset 28, sent from the speaker output of the handset 28 (the handset's speaker may be removed) via the DPDT switch 25 to the signal enhancer 26, FM transmitter 27 and finally to the earpiece headset 21 receiver where the signals are converted to acoustic waves heard by the user. Note that the RPU 23 may also include straight-forward connections to a "personal digital assistant" computer, or voice-operated devices connected to the FM receiver 24 output and not shown in FIG. 2.

RF output power of the earpiece wireless microphone 20 and RPU FM transmitter 27 may be limited by FCC regulations to a level of −47 dBm, or −47 decibels relative to a power level of one milliwatt (see 47 CFR Ch. 1, Para. 15.239, for field strength limits, and the relationship between field strength and transmitter power is discussed later with regard to the full-featured embodiment) in the 88 MHz to 108 MHz band, which is low compared to the RF power output from commercial broadcast radio stations that operate in the same band. As a result, "clear" operating frequencies for the earpiece 22 and RPU 23 (i.e., operating frequencies with suitably low interference levels) must be chosen (depending on location of use) in advance of operation to avoid interference from commercial broadcast radio stations, and also to allow operation of many units in close proximity without mutual interference. Interference problems and RF transmitter power limitations can be alleviated by operating the system in the "auditory assistance device" frequency bands near 73 MHz, where RF transmitter power can be as much as +2.8 dBm (see 47 CFR Ch. 1, Para. 15.237).

2. Full-featured embodiment

Desirable features: Many features are considered desirable for a full-featured preferred embodiment of the invention. For widespread application, it is preferred that the system allow operation of many units in close proximity without mutual interference. Occasional interference from natural or man-made sources is acceptable as long as such interference does not result in significant degradation of audio quality. Earpiece power consumption is preferably minimized to extend battery life, and use of a rechargeable battery is desirable. The earpiece is preferably smaller than the head of a cotton swab so as to be hidden from view for the majority of users. FIG. 1 depicts an earpiece 10 that provides the desired CIC form factor. The preferred embodiment should be able to operate when the earpiece 10 and RPU 16 are separated by 0.6 meter (two feet), and greater range is desirable. To allow lip reading, total delay between the arrival of an ambient acoustic signal at the earpiece microphone 12 and production of a corresponding processed acoustic signal at the earpiece speaker 15 is preferably less than 50 milliseconds. To tell where sounds are coming from (binaural localization) random left/right earpiece timing variations are preferably less than 20 microseconds. Note that larger, fixed left/right timing variations are tolerable. Microphones are preferably mounted in the earpieces (rather than body-worn) to allow stand-alone earpiece operation in the event that the primary communication link 17 between the earpiece 10 and RPU 16 is disrupted, and to preserve the user's natural direction-finding capabilities with head motion while reducing wind and clothing noise from the critical audio path. Note that auxiliary body-worn microphones (e.g., in the RPU 16) may be used to measure background noise for the purpose of automatically setting hearing aid parameters. The system's audio bandwidth (i.e., the audio signal bandwidth preserved throughout all processing and available at the speaker 15 of each earpiece 10) is preferably more than 6 KHz so that all essential speech information is preserved. See the use of articulation index in "Reference Data for Radio Engineers" to evaluate the consequences of using less than a 6 KHz bandwidth.

Choice of wireless medium: A wide variety of wireless media can be used in this invention, e.g., RF, optical (including infrared), acoustic waves (including ultrasonic), induction loop and capacitive coupling. It is possible to use any of these forms of wireless communication, as well as others not discussed in detail here (e.g., acousto-magneto resonance techniques), in the implementation of the present invention. Since induction loop and capacitive coupling wireless communication technologies are typically more suited to one-way rather than two-way communication systems, these techniques are not discussed further in reference to the present description of the preferred embodiment. Similarly, optical and acoustic wave approaches are not considered further due to the difficulties involved in providing a system which can effectively penetrate clothing. An RF approach is therefore the only approach detailed for the full-featured preferred embodiment, and one RF approach has already been described as a limited-feature embodiment.

Choice of radio frequency: Operating frequencies in the 900 MHz to 6 GHz range have long been used for electronic article surveillance (EAS) anti-theft systems and RF identification tags (see the Hewlett Packard "Communications Components Catalog" for a description of such systems and the associated components). EAS technology has a proven ability to penetrate clothing and provide a short-range wireless communication link. Operation of the full-featured preferred embodiment of the invention within this frequency range is desirable due to the availability of low-cost components. In EAS and other systems, a simple approach to RF antenna design is to provide a conductor which is one-quarter of the wavelength at the RF operating frequency (see the discussion of antenna fundamentals in "The ARRL Handbook for the Radio Amateur" for a description of the Marconi antenna). Since a quarter-wavelength antenna at 6 GHz is 1.27 cm (one-half inch) long, an antenna at this frequency can easily be disguised as an ear hair and can also serve as a hearing aid earpiece extractor 14 (although it is not required that the antenna or antennae act as an extractor nor be disguised as an ear hair). Note that frequencies lower than 6 GHz can be used (e.g., as previously described for the limited-feature embodiment), but components and antennae generally become larger. Similarly, frequencies higher than 6 GHz can also be used for the present invention but components are not as readily available. The range of frequencies near 6 GHz is therefore chosen for the present description of the preferred embodiment due to the fact that 6 GHz is the lowest frequency for which the antenna length is the same as that of a typical extractor or ear hair, and miniature components that operate in the vicinity of 6 GHz are readily available.

RF path effects: The path between the earpiece and RPU is preferably, but not necessarily, line-of-sight. To illustrate that a line-of-sight path is possible, assume the RPU is located near the user's navel. A telescoping pointer having 0.6 meter (two feet) length when fully extended can then be used to physically demonstrate that a direct line-of-sight path exists between the RPU and both earpieces for all head and body positions by placing one end of the pointer at the navel and the other end at the entry to an ear canal. As the user moves around, the pointer changes length but always defines a line-of-sight path between the RPU and earpiece positions. The transmission loss resulting from addition of a layer of clothing in the line-of-sight path (e.g., over the RPU) is minimal, and RF signals at 6 GHz are also capable of penetrating thin layers of body tissue. Specifically, the skin depth, defined as the depth at which the power of an incident RF planewave is 0.135 times its value at the surface of the skin (i.e., 8.7 dB loss), is approximately 7 mm (0.28 inch) at 6 GHz (see the "Radiofrequency Radiation Dosimetry Handbook," DTIC ADA-180678 for details). Thus, although the human body effectively blocks RF signals at 6 GHz and most of the energy is absorbed at the skin surface, RF signals to some extent penetrate the relatively thin external ear cartilage.

Figure 9:
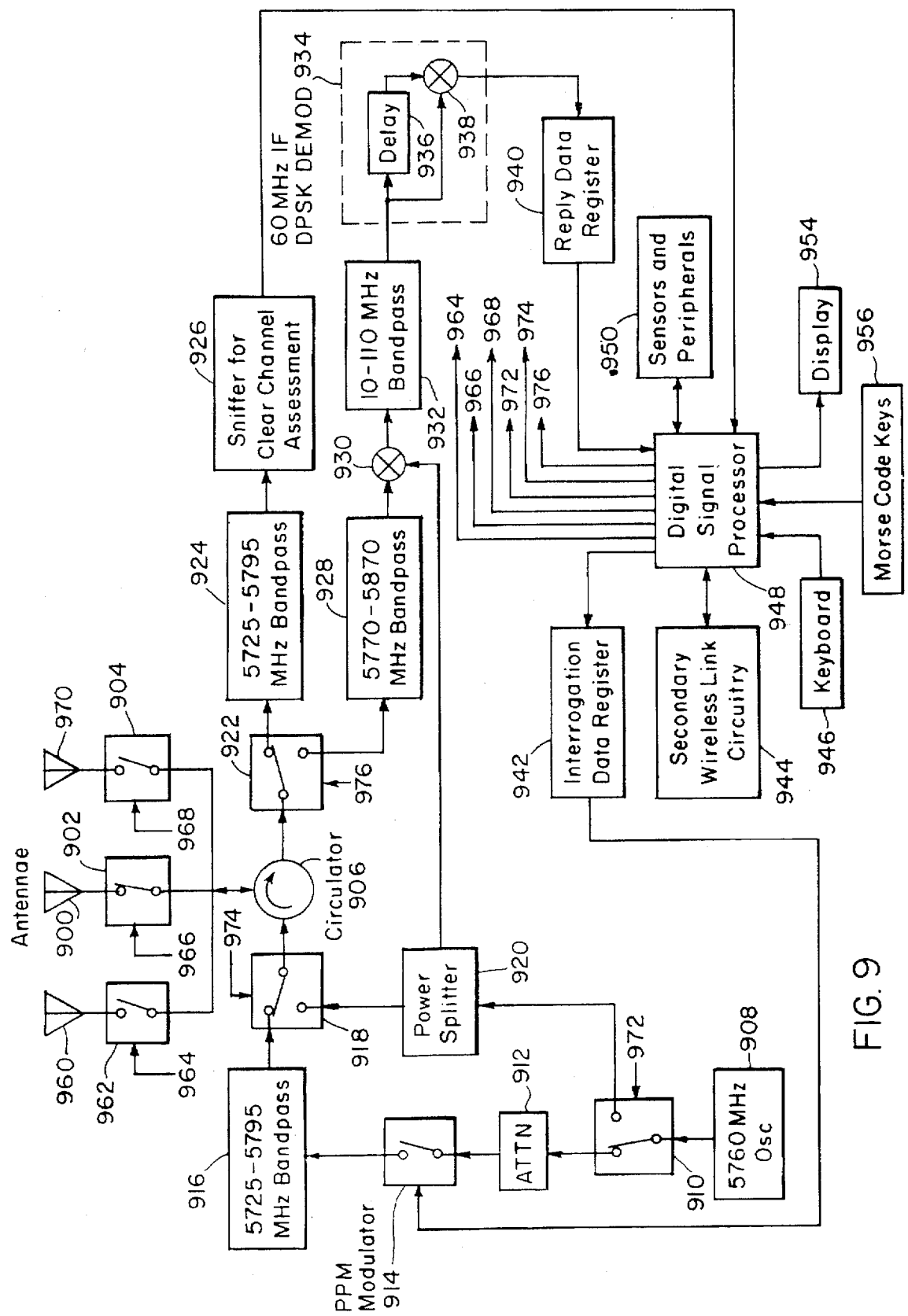
FIG. 9 is a block diagram showing details of an RPU for a full-featured preferred embodiment of the invention.

Free space path loss: Even under the assumption that a line-of-sight path exists between the earpiece and RPU, transmission power losses of 6 GHz RF signals are quite high. The free space path loss, in dB, can be expressed as 96.58+20[log(range in miles×frequency in GHz)] or 92.45+20[log(range in kilometers×frequency in GHz)]. See the discussion of space communication path losses in "Reference Data for Radio Engineers" for derivations. Approximate values for the free space path loss at 6 GHz are 47 dB at 0.9 m (3 ft), 57 dB at 3 m (9 ft) and 67 dB at 9 m (30 ft). Since a loss of 3 dB corresponds to a loss of one-half of a signal's power, and a signal which has a power level 20 dB below that of another signal has only 1% of the power of the other signal, a 6 GHz signal received at a range of 9 m (30 ft) has only 1% of the power of a signal received at a range of 0.9 m (3 ft) when isotropic (omni-directional) antennae are used at the transmitter and receivers. In many systems, path losses are overcome by use of highly directional antennae which provide additional gain (typically +28 dB for each antenna, with one antenna at the transmission end and another at the reception end of a link). For application in the present invention, however, physically large high-gain antennae are unacceptable. Techniques that use small antennae to reduce transmission path losses are applicable to the present invention, especially in the RPU, and many schemes are possible. For example, FIG. 9 shows a simple approach in which three antennae are positioned at various orientations in the RPU, and more antennae may be used if desired. Antenna 900 is selected by switch 902 (under the control of digital signal processor DSP 948 via control signal 966), while antenna 960 is deselected by switch 962 (under the control of DSP 948 via control signal 964) and antenna 970 is deselected by switch 904 (under the control of DSP 948 via control signal 968). The RF switches 902, 904 and 962 may be fabricated, for example, using PIN diodes well known in the art. The antenna selection process, known in the art as "diversity switching," is automatically controlled by the DSP 948, and the antenna that yields the best link reliability (as indicated by the fewest parity errors, described later) is selected by the DSP 948 for use. Other techniques well known in the art, e.g., electronically steered phased arrays, can also be used.

Operating power limitations: Operation in many frequency bands is possible as long as the applicable requirements are met. A frequency band slightly below 6 GHz, the 5725 to 5875 MHz ISM (industrial, scientific and medical) band, is used here to illustrate the operation of a full-featured preferred embodiment. Non-licensed operation in this band is governed in the United States by 47 CFR Ch. 1, Para. 15.249, and other restrictions may apply depending upon the country in which the invention is used. For the present discussion, only the constraints imposed on operation by the United States Federal Communications Commission are considered. In the 5725 MHz to 5875 MHz ISM band, the average field strength at three meters must be less than 50 mV/meter. For an isotropic radiator, the power in watts is expressed as 3.33% of the square of the product of the field strength in V/meter and the range in meters. See the section on antennas, especially with regard to field strength and radiated power from antennas in free space, in "Reference Data for Radio Engineers," as well as Annex K of the "Manual of Regulations and Procedures for Federal Radio Frequency Management" for derivations. For the stated range of three meters and field strength of 50 mV/meter, the average power limit is 0.75 mW (−1.25 dBm). A peak field strength value 20 dB (a factor of 10) higher is allowed (500 mV/meter), which leads to a peak power limit of 75 mW (+18.75 dBm). Other restrictions also apply, but these restrictions are easily met by standard design practices (see 47 CFR Part 15, Subpart C-Intentional Radiators).

Potential interference sources: Although the regulations governing operation of devices in the ISM band near 6 GHz limit RF transmission power to relatively low levels, such limitations help ensure that other equipment is unlikely to interfere. Interference from other nearby hearing aids is eliminated through a time-division multiplexing scheme described later in this section. Interference from reflections of signals off distant surfaces (known as "multipath" in the art) is eliminated by the round-trip free space path loss. The relatively low data rate used in the invention gives immunity to reflections from nearby surfaces. Interference from other nearby low-power equipment is minimized by the free space path loss described earlier. Interference from high-power ISM equipment (typically point-to-point communication links with high-gain antennae) is eliminated by the user moving out of the narrow high-power beam. A proposed European automotive electronic toll collection system would use high-power pulses at 5.8 GHz, but the cars are in motion and provide shielding. High-power weather radars such as those found at airports and used by television stations operate below 5650 MHz, which is 75 MHz below the ISM band of interest. Thus, at the present time, the ISM band near 6 GHz is a reasonable choice for operation of this non-licensed equipment.

RF system operation: Knowledge of the art of avionics design, especially the Mode S air traffic control secondary radar system (see "U.S. National Aviation Standard for the Mode Select Beacon System, Appendix 1 to DOT FAA Order 6365.1A"), is an aid to understanding the full-featured embodiment of the invention. In the Mode S air traffic control system, a ground-based equipment known in the art as an interrogator transmits a signal known in the art as an interrogation to individually query devices known in the art as transponders (transmitter responders) that are carried by aircraft. Receipt of a properly addressed interrogation by a transponder (i.e., the address bits in the interrogation match the transponder's internal address) elicits a signal known in the art as a reply, which is transmitted by the transponder and received by reply processing circuitry at the interrogator. A transponder is therefore a specialized type of transceiver which only transmits (responds) after successfully receiving an appropriate interrogation. In the hearing aid system shown in FIG. 1, the RPU 16 contains, among other circuitry, an interrogator system and reply processor suitable for the generation and reception of digital microwave signals. Note that although analog modulation techniques well known in the art (e.g., frequency modulation as used in the limited-feature embodiment) could also be used in a full-featured embodiment, only digital techniques are detailed here. Each earpiece 10 contains a transponder (the transceiver 13 in this example) that generates a reply in response to a correctly addressed interrogation. Interrogations from the RPU 16 interrogator to the earpiece 10 transponder 13 over the primary RF link 17 consist of a synchronizing pulse, left/right (L/R) selection bit, transponder address, audio data from the RPU 16 to the earpiece 10, an auxiliary bit (described later in this section) and an unmodulated carrier interval. Replies from the earpiece 10 transponder 13 to the RPU 16 reply processor contain a synchronizing pulse, audio data from the earpiece 10 to the RPU 16, an auxiliary bit and a parity bit. Using the technique described here, no interrogator address is needed, the transponder generates replies by modulating the unmodulated carrier from the interrogator, and no microwave (6 GHz) oscillator nor amplifier is required in the earpiece 10 transponder 13. Although it is physically possible to use a microwave oscillator or amplifier in the earpiece 10 transponder 13, and there may be some advantage to doing so in certain instances, the full-featured preferred embodiment described here avoids placing such devices in the earpiece 10 to minimize size and power consumption. Note that the limited-feature embodiment of FIG. 2 uses oscillators and amplifiers in the earpiece 22 wireless microphone 20 and headset 21. In some applications it may be desirable to use multiple RPUs that communicate with each other. In such applications, each RPU may contain, for example, a complete addressable transponder as part of the RPU's internal circuitry. The communication between RPUs is then performed in the same manner as communication between an RPU and earpiece described here.

Figure 3:
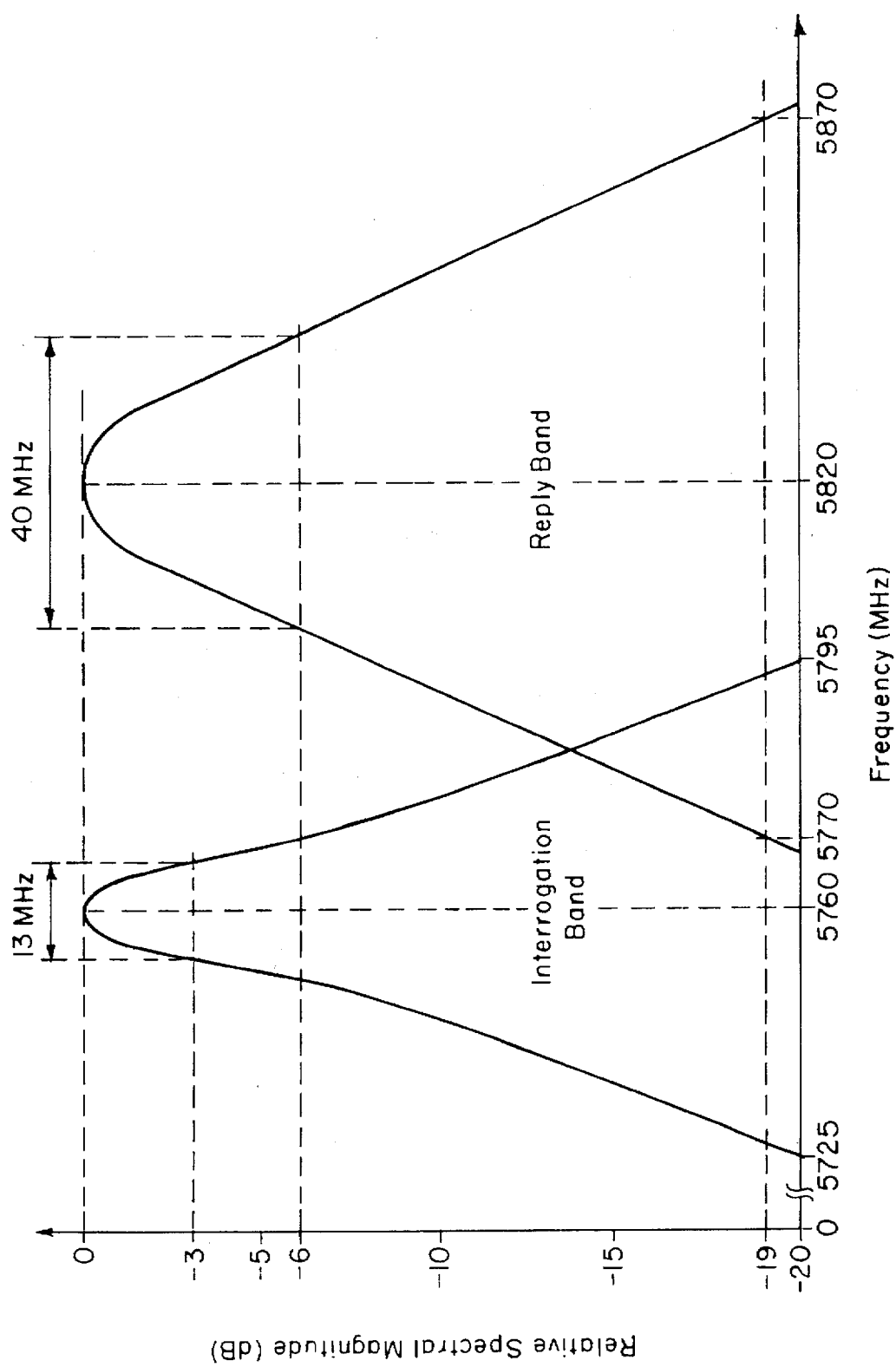
FIG. 3 is a relative spectral magnitude plot showing the frequency domain characteristics of a wireless link used in a full-featured preferred embodiment of the invention.

Interrogation and reply frequency bands: One of many differences between the Mode S system and the full-featured preferred embodiment of the hearing aid system is the operating frequency. While the Mode S system uses a center frequency of 1030 MHz for interrogations and 1090 MHz for replies, the hearing aid uses 5760 MHz for interrogations and 5820 MHz for replies, as shown in the relative spectral magnitude plot of FIG. 3. In both the typical hearing aid and Mode S systems, however, the intermediate frequency (IF) is 60 MHz (the difference between the interrogation and reply center frequencies) to allow use of standard miniature components. Another difference is that Mode S replies use PPM (pulse position modulation) at a 1 MHz data rate resulting in a 2.6 MHz 3 dB bandwidth and 14 MHz 20 dB bandwidth, while the hearing aid interrogations use PPM (to simplify the earpiece transponder RF design) at a 5 MHz data rate resulting in a 13 MHz 3 dB bandwidth and 70 MHz 20 dB bandwidth as shown in FIG. 3. Note that the bandwidths stated are known in the art as signal bandwidths, and use of RF or IF filters which diminish these bandwidths may cause signal waveform degradation, while use of greater bandwidths increases the likelihood of degradation due to noise and interference. Mode S interrogations use DPSK (differential phase shift keying) at a 4 MHz data rate resulting in an 8 MHz 6 dB bandwidth and 20 MHz 19 dB bandwidth, while the hearing aid replies use DPSK (for superior noise immunity at low power levels) at a 20 MHz data rate resulting in a 40 MHz 6 dB bandwidth and 100 MHz 19 dB bandwidth as shown in FIG. 3. Note that during the earpiece transponder reply, the RPU interrogator transmits an unmodulated carrier pulse at 5760 MHz which, due to its narrow bandwidth, does not interfere with the reply signal information contained in the 5770 MHz to 5870 MHz 19 dB signal bandwidth. Other modulation techniques (e.g. frequency shift keying) could easily be used instead of the techniques described here, however the modulation techniques described here were chosen for a full-featured preferred embodiment description on the basis of widespread use, wealth of documentation and component availability. Similarly, data rates, power levels, interrogation frequencies, reply frequencies and intermediate frequencies other than those described here could also be used.

Figure 4:
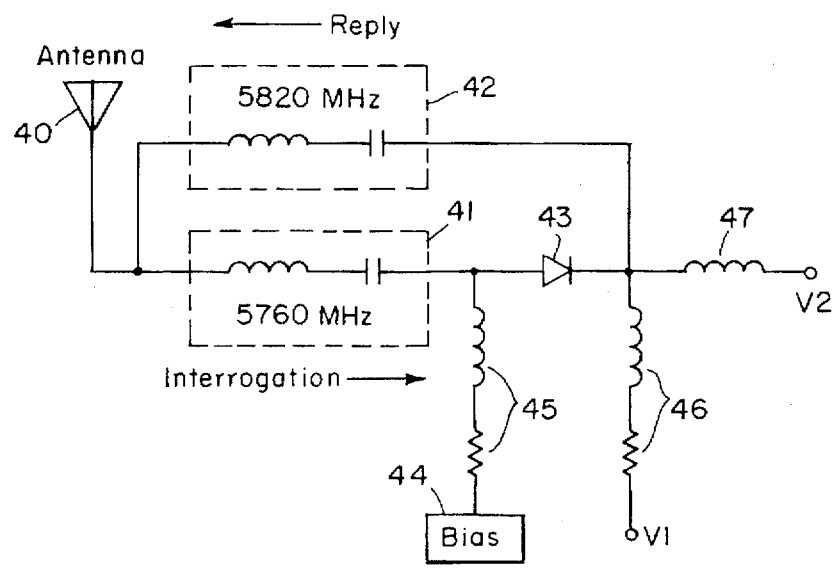
FIG. 4 is a simplified schematic of the earpiece transponder (transmitter responder) RF circuitry used to illustrate operation of a full-featured preferred embodiment of the invention.
Figure 8:
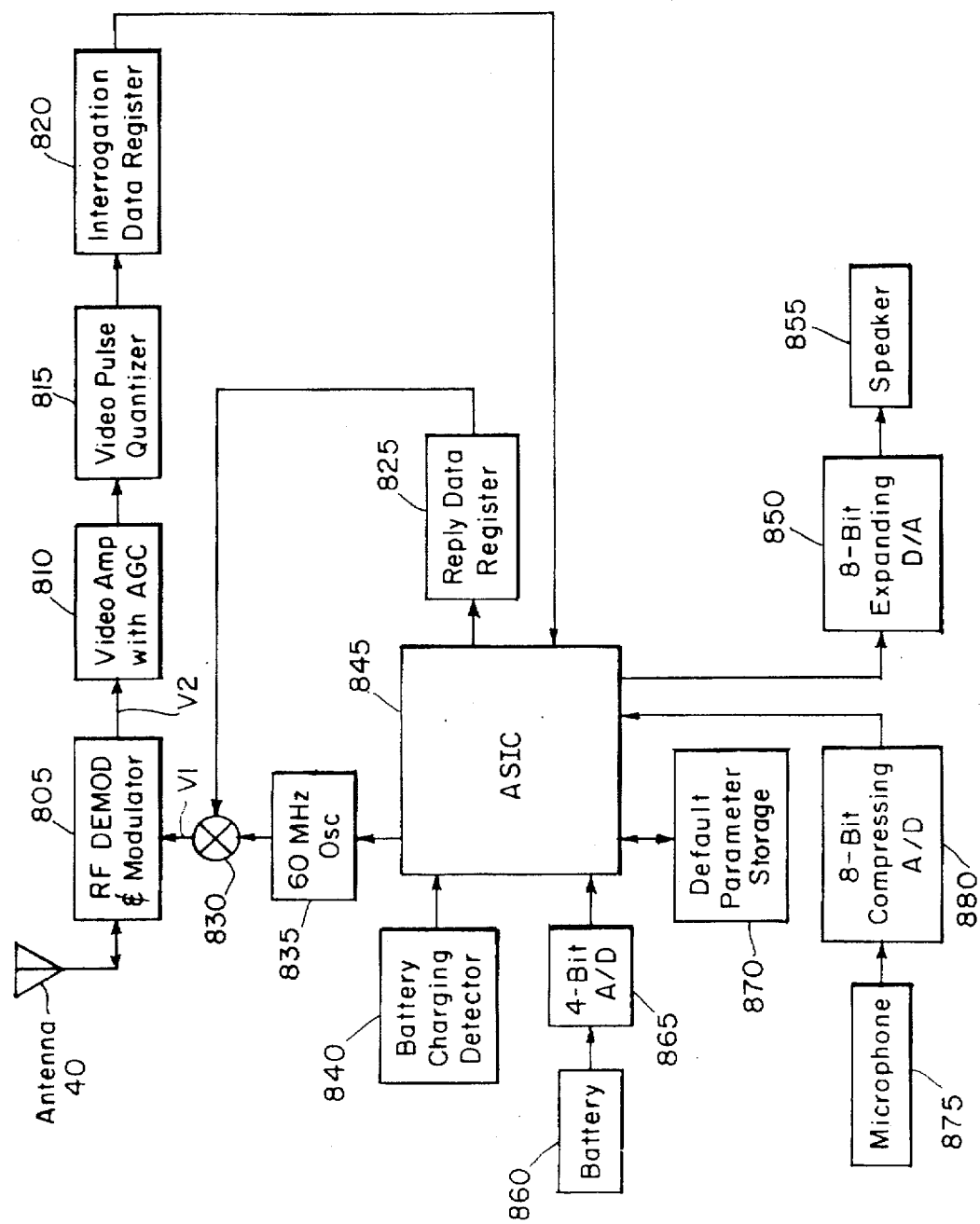
FIG. 8 is a block diagram showing details of an earpiece for a full-featured preferred embodiment of the invention.

Earpiece transponder RF circuitry simplified schematic and operation: A simplified schematic for typical earpiece transponder RF circuitry is shown in FIG. 4. The function of the circuitry in FIG. 4 is shown in the overall earpiece block diagram of FIG. 8 as RF demodulator and modulator 805. Although the function of RF demodulator and modulator 805 can be implemented using other circuits well known in the art, only the circuit of FIG. 4 is used here for explanatory purposes. For simplicity, impedance transformer matching sections are not shown (see "The ARRL Handbook for the Radio Amateur" for a discussion of quarter-wave transformers), and such transformers do not occupy significant volume. A single quarter-wave Marconi antenna 40 (shown in both FIG. 4 and FIG. 8) with horizontal polarization (due to its orientation exiting the ear canal) is used both for interrogations and replies, although other antenna configurations are possible. In this example, the antenna 40 is a quarter wavelength at 5790 MHz, which is halfway between the interrogation center frequency of 5760 MHz and the reply center frequency of 5820 MHz, resulting in a small mismatch loss. The antenna 40 is of a length which can be useful in the role of earpiece extractor if desired. The series resonant circuits 41 and 42 are actually high-Q dielectric resonators which present a low impedance at resonance and a high impedance otherwise. These resonators may be custom-fabricated from high dielectric constant materials, and are suitable for direct mounting in microstripline circuits (see Dielectric Laboratories' CAPCAD catalog for design information). The resonators have typical dimensions of 0.25 mm (0.01 inch) thickness, 0.5 mm (0.02 inch) width and 2.5 mm (0.1 inch) length. To illustrate circuit operation, first assume that the earpiece transponder is not detecting any interrogations and is not in the process of transmitting a reply. Specifically, with reference to FIG. 5, assume that the earpiece circuitry is in its quiescent state during a time which is neither an interrogation interval 50 nor a reply interval 52. Only a small amount of power is required by the transponder RF circuitry in its quiescent state, and in this state the transponder is continuously searching for a synchronizing pulse from an RPU interrogator. The medium barrier Schottky diode 43 (e.g., HP 5082-2207) is slightly forward biased by a fixed bias voltage 44 applied to the diode 43 through an associated RL (resistance-inductance) network 45. Note that a zero bias diode (e.g., HP HSMS-0005) could be used if desired, eliminating the need for a bias voltage 44 and its associated RL network 45. The voltage at V1, which is applied to the diode 43 through another RL network 46, has a value near ground (zero volts) at all times except during the reply interval 52. When interrogation PPM RF pulses are received, they are detected by the Schottky diode 43 and subsequently appear at voltage point V2, through an inductor 47, as baseband video pulses. Typical pulses appearing at V2 are shown in FIG. 5 as the interrogation interval 50 portion of an RPU interrogation 51. The PPM interrogation baseband video pulses are processed by a video amplifier 810 and subsequent video pulse quantizer circuitry 815, well known in the art and not described in detail here (see the "TCAS Experimental Unit Hardware Description," NTIS ADA-169870, for details of such circuitry applied in the Mode S system), to obtain bits for storage in the interrogation data register 820. Due to the relatively limited dynamic range required of the video amplifier 810, the logarithmic amplification often used the Mode S system is not typically necessary in the hearing aid application, and automatic gain control (AGC) circuitry may be used instead. After completion of the interrogation interval 50, the RPU interrogator transmits an unmodulated 5760 MHz carrier pulse for the duration of the reply interval 52. During the reply interval 52, a modulated (via modulator 830) low-power 60 MHz oscillator 835 is applied to voltage point V1, causing the diode 43 to turn on and off at a 60 MHz rate and act as a mixer. The mixer diode 43 generates frequency components centered at the difference frequency of 5700 MHz and the sum frequency of 5820 MHz. The 5820 MHz sum component passes through the resonator 42, and forms the reply which is wirelessly transmitted from the earpiece transponder antenna 40 to the RPU reply processor circuitry. The earpiece 60 MHz oscillator 835, which is only turned on during the reply interval, changes phase at specified points in time to generate the DPSK reply data. Details of this operation are shown in FIG. 8, where the 60 MHz oscillator 835 output is phase modulated by modulator 830 (i.e., multiplied by the value +1 or −1 depending on the values of DPSK encoded bits, using the encoding technique described later, stored in the reply data register 825) prior to its application to the RF modulator circuitry 805. Note that all earpiece functions (e.g., power control for the 60 MHz oscillator 835) are controlled by a custom application-specific integrated circuit (ASIC) 845. The ASIC 845 may be a low-power low-voltage device similar, e.g., to the ECI Semiconductor P576 custom programmable linear/digital gate array. Many of the functions that are shown as separate blocks for clarity in FIG. 8, e.g., reply data register 825, may be implemented within the ASIC 845.

Remote processor unit interrogator and reply processor: The RPU, shown in FIG. 9, may use any of a wide variety of components well known in the art. The DSP 948 may contain several integrated circuits, e.g., the Motorola DSP56L002 single-chip digital signal processor, a Motorola DSP56200 cascadable-adaptive digital filter chip and supporting memory devices well known in the art. Miniature components such as dielectric resonance oscillators are available for the microwave oscillator 908, and the DPSK replies can be decoded using surface acoustic wave (SAW) or glass bulk acoustic wave (BAW) delay lines 936 in a standard delay-and-multiply demodulator circuit 934. An alternative demodulator that achieves superior noise immunity can be implemented using a phase-locked loop in a squaring loop configuration for carrier recovery instead of delay-and-multiply circuitry 934. Decoding of a DPSK waveform using such coherent detection techniques is known in the art as differentially encoded coherent phase shift keying, or DECPSK. Amplifiers using low noise pseudomorphic high electron mobility transistors (e.g., the HP ATF-36077) may be used as needed (e.g., between the circulator 906 and routing switch 922), and such amplifiers are not individually identified in FIG. 9. All switches shown in FIG. 9 are RF switches that can be implemented using, e.g., PIN diodes. Switch control connections from the DSP 948 to the RF switches are shown in FIG. 9 for clarity, and all switches remain set as shown until changed as noted. The system shown in FIG. 9 demodulates a received reply when the RF reply travels through a selected antenna 900, antenna selection switch 902, circulator 906, routing switch 922 (set to the position opposite that shown in FIG. 9 during the reply interval by DSP 948 via control signal 976), bandpass filter 928 and IF mixer 930. The IF mixer 930 downconverts the reply by mixing it with a small amount of RF power from the 5760 MHz oscillator 908 via switch 910 (which is set to the position opposite that shown in FIG. 9 during the reply interval by DSP 948 via control signal 972) and power splitter 920. The resulting DPSK reply has a center frequency of 60 MHz, a bandwidth of 100 MHz, and is passed through the bandpass filter 932 to the DPSK demodulator 934 which, in this example, consists of a 50 nsec delay line 936 and multiplier 938. The resulting bits are stored in the reply data register 940 for processing by the DSP 948.

Time-division multiplexing: In the embodiment of the invention detailed here, all RPU interrogators share one frequency band centered, for example, at 5760 MHz for interrogations, while all earpiece transponders share another frequency band centered, for example, at 5820 MHz for replies. The interrogations (and therefore the replies also) in the embodiment detailed here are timed to avoid "collisions" through the use of time-division multiplexing techniques. Each RPU contains a circuit known in the art as a "sniffer," operational only when the RPU interrogator is not transmitting, that detects the presence of other interrogators. This process is known in the art as "clear channel assessment." The sniffer circuit (which, for this example, may consist mainly of a Schottky diode and other circuitry similar to that used in an earpiece transponder) allows the RPU to determine whether or not other interrogators are nearby, as well as the time intervals during which nearby interrogators are transmitting. As shown in FIG. 9, this result is achieved when RF interrogations from other units travel from a selected antenna 900 through an antenna selection switch 902, circulator 906, routing switch 922 and bandpass filter 924 to the sniffer 926, which indicates the presence of other interrogators to the DSP 948. Time is divided into "slots," where a slot is defined as a time interval of specific duration, with a single interrogation/reply cycle taking place in a single time slot. With reference to FIG. 5, one time slot consists of the duration of an interrogation interval 50 and the corresponding reply interval 52. Whenever possible, an interrogator transmits in an otherwise unoccupied time slot immediately following some occupied time slot, with an average repetition frequency that depends on the audio signal sampling rate (described later in this section). Using this approach, many interrogators and transponders can operate in close proximity without the need to share any time slots. The presence of interference, as detected by the RPU, is indicated by a high reply failure rate (a parity error or no response from a selected transponder). After a certain number of reply failures (e.g., 1% in any 0.05 second interval) the interrogator switches to an unoccupied time slot immediately following the reply from a randomly selected nearby system (if any nearby system is detected). If no unoccupied time slot is available, the interrogator transmits a single interrogation in an occupied slot selected at random until successful communication is established with the desired transponder. A different RPU antenna may also be selected to aid establishment of a reliable link between the RPU interrogator and the selected earpiece transponder. When the RPU interrogator must communicate with more than one earpiece transponder, the time slot and antenna selection information is stored in the RPU DSP 948 separately for each transponder. The time slot selection procedure may or may not force other interrogators to change their time slot selections due to interference, depending on relative geometry considerations described later in this section. For all cases, however, the procedure just described allows large numbers of similar units to operate in close proximity even under conditions of worst-case mutual RF interference geometry.

Waveform design: Those skilled in the art will realize that a very large number of waveform designs are possible, and a discussion of the various techniques (including spread-spectrum, code-division multiple-access and frequency-hopped waveforms) is beyond the scope of this document. Operation of the invention can best be illustrated by considering the waveform examples presented in FIG. 5, with the full realization that many other waveforms are possible. During the interrogation interval 50, which has a duration of 5600 nsec, the RPU transmits a 5 Mbits/sec PPM interrogation waveform, the amplitude envelope vs. time diagram 51 of which is shown in FIG. 5. The interrogation consists of a series of RF pulses having duration of either 100 nsec or 200 nsec, center frequency of 5760 MHz and power level of +1.3 dBm (1.35 mW). A block diagram of the circuitry for generating the desired interrogation waveform is shown in FIG. 9, where the 5760 MHz oscillator 908 output is routed by a switch 910 to an attenuator 912 that sets the interrogation level. The PPM portion of the interrogation waveform 51 is generated during the interrogation interval 50 when serial binary data from the interrogation data register 942 causes a switch 914 to turn on and off. The resulting RF waveform is filtered 916, routed to a circulator 906 by means of a switch 918, and sent through another switch 902 to a selected antenna 900. No signal is transmitted from the earpiece during the interrogation interval 50. During the reply interval 52, the RPU interrogator transmits a single unmodulated RF pulse having 550 nsec duration, center frequency of 5760 MHz and power level of 16.8 dBm (48 mW). This pulse is generated when the 5760 MHz oscillator 908 output is routed through a switch 910 (set to the position opposite that shown in FIG. 9 during the reply interval by DSP 948 via control signal 972), power splitter 920, another switch 918 (set to the position opposite that shown in FIG. 9 during the reply interval by DSP 948 via control signal 974), circulator 906, and antenna selection switch 902 to the selected antenna 900. Each time slot, defined as the duration of a single interrogation/reply cycle, is 6150 nsec. During the reply interval 52, the earpiece transmits a 20 Mbits/sec DPSK reply waveform, the amplitude envelope vs. time diagram 53 of which is shown in FIG. 5. The reply consists of a single RF pulse having 550 nsec duration with possible phase reversals at 50 nsec intervals, center frequency of 5820 MHz and power level of approximately −37 dBm (0.0002 mW). For a monaural system (one RPU and one earpiece), an interrogation/reply cycle occurs once every 80 microseconds (12.5 KHz repetition frequency). For a binaural system (one RPU and two earpieces), two interrogation/reply cycles (one for each earpiece) occur within every 80 microsecond interval, for an average of one interrogation/reply cycle every 40 microseconds (25 KHz average repetition frequency). For design simplicity, all timing is linked to the 60 MHz IF in this description of the invention. Specifically, three periods of a 60 MHz waveform have a total duration of 50 nsec, and multiples of 50 nsec intervals are used in the timing of both the PPM and DPSK data. The average repetition period is 1600×50 nsec=80 microseconds. The interrogation center frequency is 60 MHz×96=5760 MHz and the reply center frequency is 60 MHz×97=5820 MHz. Thus, given a single oscillator with an appropriate frequency (e.g., 1 MHz) all other required system frequencies can be generated by appropriate frequency division (e.g. 25 KHz is 1 MHz divided by 40) or frequency multiplication (e.g., 60 MHz is 1 MHz multiplied by 60).

Interrogation data format: The interrogation 51 begins with a 100 nsec "gap," or guard interval during which no RF transmissions occur, preceding the first pulse. The gap ensures that the leading edge of the first interrogation pulse can be clearly detected, and allows adequate time for a preceding reply pulse from any nearby system to decay to an undetectable level. The first interrogation pulse has a duration of 100 nsec, and is followed by a 300 nsec interval during which no RF transmission occurs. This forms a unique pulse sequence, known in the art as a sync pulse, which is used for PPM synchronization purposes. The remaining PPM data pulses occur within regular, uniform 200 nsec bit intervals. If the data bit value is a logic "1," an RF pulse is transmitted in the first 100 nsec but not the last 100 nsec of the bit interval. Similarly, if the data bit value is a logic "0," an RF pulse is transmitted in the last 100 nsec of the bit interval but not in the first 100 nsec of the bit interval. The first data bit, designated L/R, indicates whether a left or right earpiece is addressed. If the L/R bit is a logic "1," a left earpiece is addressed, and a right earpiece is addressed if the L/R bit is a logic "0." Note that a right (left) earpiece will immediately cease processing upon detection of an interrogation addressed to a left (right) earpiece, and will then begin searching for another sync pulse. As shown in FIG. 8, processing of bits in the interrogation data register 820 takes place, for example, in the earpiece ASIC 845. Placing the L/R bit first in the data stream allows 50% of all earpieces within the range of a given interrogator to cease processing the interrogation at the earliest possible opportunity. Following the L/R bit is a 15-bit address, for which the most significant bit is transmitted first. The earpiece ASIC 845 decodes the L/R bit as well as the address and, upon detection of a mismatch with its internal pre-assigned L/R bit or address (which are stored in the default parameter storage 870), ceases processing the interrogation at the earliest possible opportunity. The 15-bit address corresponds to the user's birth day and "year modulo 89" to obtain a relatively uniform distribution of address codes throughout the general population. An address in which all of the bits are zeros or ones is not allowed, as an all zeros or ones condition is often indicative of a system failure. A user born on Jul. 20, 1969, will have an address of one, a user born on Jul. 21, 1969, will have an address of two and so on for a total of 32,508 days (approximately 89 years), when the sequence starts over again. Since the fifteen address bits allow representation of 32,768 different numbers, the 258 otherwise unused address codes can be reserved for special functions such as "broadcast" mode interrogations from fixed-location RF transmitters for delivery of special information services to the handicapped. Note that the reserved codes can also be used in a procedure (described later in this section) that allows wireless location of misplaced system components, such as cochlear implant electrode driver units, which may not transmit a signal under normal operating conditions. Although the addressing scheme described here does not ensure total privacy, the combination of a 15-bit address and short communication range makes the system more private than most cordless telephones that use an 8-bit address (see 47 CFR Ch. 1, Para. 15.214). Note that the address can be changed by the user, if desired, using a procedure described later in this section that involves one of the reserved address codes. The 15-bit address is followed by an 8-bit audio data field, for which the most significant bit is transmitted first. The audio data is an 8-bit companded (compressed/ expanded) sample, representing one value of an audio waveform sampled at the 12.5 KHz repetition frequency described earlier, resulting in a 100 Kbits/sec effective audio data rate between the RPU and each earpiece. Those skilled in the art will recognize that many other audio waveform data formats are possible, ranging from the 4.8 Kbits/sec code excited linear prediction (CELP) techniques of Federal Standard 1016 to the 2.1168 Mbits/sec format commonly used in audio compact disc (CD) players. The 100 Kbits/sec data format chosen for this description of the full-featured preferred embodiment allows use of a simple data encoding approach applicable to all types of sounds, including speech and music. Unlike systems that use more complicated circuitry to achieve lower data rates, companding allows use of a simple encoder and decoder in the earpiece (see the discussion of instantaneous companding in "Digital Processing of Speech Signals" by L. R. Rabiner and R. W. Schafer, Prentice-Hall, Inc., 1978). The 8-bit companded audio data typically provides the perceptual equivalent of 11-bit uniform quantization. System details are shown in FIG. 8, where a microphone 875 is connected to an 8-bit compressing analog-to-digital (A/D) converter 880, and the resulting digital sample is input to an ASIC 845 used to control the earpiece functions. The ASIC 845 subsequently places the data sample in the reply data register 825. Similarly, the ASIC 845 reads data from the interrogation data register 820 and transfers the samples to an 8-bit expanding digital-to-analog (D/A) converter 850 connected to the earpiece speaker 855. The 12.5 KHz repetition frequency allows faithful reproduction of all audio frequency components below 6 KHz, while providing an additional 250 Hz (i.e., 4%) guard band for anti-aliasing filters (built into the A/D 880 and D/A 850 converters). Note that occasional data errors are typically undetectable by the human auditory system, so no error correction or re-transmission of audio data is required. The 8-bit audio data field of the interrogation is followed by a 1-bit auxiliary data field for low-rate critical non-audio data. Auxiliary data bit values from many successive interrogations are assembled in an internal register of the earpiece ASIC 845 to form a message of any desired length (i.e., any reasonable number of bits), and such messages can be echoed back to the RPU interrogator (and DSP 948) from the earpiece transponder (under control of the ASIC 845) for verification if desired and re-transmission if necessary. Information such as default settings for the earpiece, as described later, is communicated via the interrogation auxiliary link. The format of the auxiliary link data in this particular implementation of the preferred embodiment is similar to the pulse format used for PPM data transmission. Specifically, an auxiliary link message begins when the synchronization sequence "1,0,0,0" is received as a result of the ASIC 845 assembling the auxiliary bits from four successive interrogations. Receipt of the sequence "1,0" ("0,1") by assembling the auxiliary bits from the next two interrogations, respectively, indicates a logic "1" ("0") for the first auxiliary link message bit, and likewise for other bits until the next synchronization sequence is encountered. It will be clear to those skilled in the art that many industry-standard data link protocols can be used on the auxiliary data link, but a discussion of such protocols is beyond the scope of this document. After transmission of the auxiliary bit, the interrogator inserts a 100 nsec gap during which the higher RF power output circuitry is enabled for the unmodulated reply interval 52 pulse (i.e., switch 914 is opened while switches 910, 918 and 922 are all set to the position opposite that shown in FIG. 9). The 100 nsec gap at the end of the interrogation interval 50 also allows turn-on time for the 60 MHz oscillator 835 in the earpiece transponder, as controlled by the ASIC 845.

Reply data format: The reply 53 from a correctly addressed earpiece transponder begins with a 50 nsec transmission for DPSK data synchronization (DPSK sync). Specifically, if a delay-and-multiply demodulator 934 is used in the RPU reply processor, the delay line 936 must be initialized by the DPSK sync transmission to properly decode subsequent DPSK data. The DPSK sync and subsequent data bits occur within regular, uniform 50 nsec bit intervals. The DPSK data bit encoding technique used in this particular implementation is as follows: if preceded by a phase reversal, a bit interval represents a logic "1" (otherwise the bit interval represents a logic "0"). An 8-bit audio data field follows the DPSK sync, and the most significant bit is transmitted first to reduce the impact of any errors caused by interfering pulses. The 8-bit audio data is companded as previously described for the interrogation data format. The audio data is followed by an auxiliary data bit, which is similar in form and function to the interrogation auxiliary data bit described earlier. Information such as the earpiece battery voltage level is communicated via the reply auxiliary link. For example, the earpiece battery 860 voltage can be sampled using a 4-bit A/D converter 865, and the resulting data input to the ASIC 845 for inclusion in the reply auxiliary link comprising the auxiliary data bit in many sequential replies. The last bit of each reply is a parity bit, used for interference detection (described earlier), that is computed by logic in the earpiece ASIC 845. The value of the parity bit is computed using all audio and auxiliary data bits received in the interrogation 51 and transmitted in the reply 53. Odd parity is used to ensure that at least one reply bit has a logic "1" value, so that a reply without any phase reversals indicates an earpiece malfunction. A parity error occurs when the odd parity bit generated in the RPU DSP 948 using all audio and auxiliary data bits transmitted in the interrogation 51 and received in the reply 53 does not match the received reply parity bit. Note that the interrogation and reply formats described here are relatively inefficient from the standpoint that although the equivalent of 39 bits are transmitted for each interrogation/reply cycle, only 18 of those bits are used for the transfer of data. It will be clear to those skilled in the art that many more efficient formats are possible. For example, the 8-bit audio data fields for the interrogation 51 and reply 53 could both be doubled to create 16-bit audio data fields, with each field containing two 8-bit samples, and the resulting interrogation/reply repetition frequency could be halved (while keeping the audio sampling frequency constant at 12.5 KHz). The formats used here, however, are for illustrative purposes and lead to a simple implementation of the full-featured preferred embodiment.

RF transmission power restrictions: The full-featured embodiment of the invention described here is designed for non-licensed operation under 47 CFR Ch. 1, Para. 15.249. As discussed earlier, RF power radiated from the system must not exceed 0.75 mW average and 75 mW peak. Power radiated from the earpiece transponder, typically 0.2 microwatt in this version of the full-featured preferred embodiment, is negligible. The 48 mW peak RPU transmission power is well below the 75 mW limit. Note that a sinusoidal waveform having a peak-to-peak voltage of 4.5V placed across a 50 ohm load dissipates 50 mW, so batteries suitable for the RPU interrogator (e.g., 9V) are widely available. The RPU transmits an interrogation once every 0.04 msec, on the average, for worst-case binaural operation. The allowable energy in each interrogation/reply cycle is therefore 0.75 mW×0.04 msec=0.03 microjoule. The RF energy actually transmitted by the RPU is 26×0.0001 msec× 1.35 mW=0.00338 microjoule during the interrogation interval and 0.00055 msec×48 mW=0.0264 microjoule during the reply interval, for a total of 0.02978 microjoule in each interrogation/reply cycle (which is less than the allowable limit of 0.03 microjoule). The average worst-case RPU transmission power is therefore (0.02978 microjoule)/(0.04 msec)=0.7445 mW, which is below the 0.75 mW average power limit. According to ANSI/IEEE Standard C95.1-1991, the maximum permissible exposure to 6 GHz RF radiation is 4 mW per square centimeter averaged over fifteen minutes, and exposure to the eyes and testes should be avoided. Exposure from the system described here falls far below the permissible limit when standard design practices well known in the art are followed. Exposure also falls well below the 1 mW per square centimeter level which is believed to be safe indefinitely (see the Microwave Radiation Hazards section of "Reference Data for Radio Engineers").

RF link power budget: Using the formulae stated earlier, the free space path loss for the 5760 MHz interrogation over a distance of 0.6 meter (two feet) is approximately 43 dB. Since the interrogation power level transmitted at the RPU is +1.3 dBm, the interrogation power level received at the earpiece transponder is approximately +1.3 dBm–43 dB=–41.7 dBm. To ensure a reliable link under all possible physical configurations, multiple RPU dipole antennae in different orientations with diversity switching are desirable (i.e., as shown in FIG. 9, the antenna 900 which best communicates with the earpiece is selected by a switch 902 under control of the DSP 948). Circular polarization antenna techniques may also prove useful depending upon the orientation of the earpiece relative to the RPU (e.g., carrying the RPU on a belt near the navel vs. carried in a pocket). See the discussion of circular polarization in "The ARRL Handbook for the Radio Amateur" for details. Such RPU antenna considerations well known in the art are necessary to ensure that the link loss does not exceed acceptable levels, and it is highly desirable to direct radiated RF energy from the RPU towards the earpiece and away from the user's body to the maximum extent possible. An interrogation level of –42 dBm for the PPM pulses received at the earpiece transponder is more than adequate to operate the transponder detector diode (diode 43 in FIG. 4), which has a typical tangential sensitivity of –54 dBm, giving a 12 dB SNR (signal-to-noise ratio) for the interrogation. During replies, the detector diode 43 acts as a mixer using on/off modulation. It can be shown that on/off modulation causes a conversion loss of 10 dB, i.e., the desired output signal voltage is less than the input signal voltage by a factor of approximately 3.14 (see the function-product relation formulae for use in trigonometry, and the Fourier expansion for a square wave in the "CRC Standard Mathematical Tables" for derivations). Although this loss is considerably greater than the 7 dB conversion loss typically associated with double-balanced mixers, the single-diode approach used here is capable of operation using very low power drive levels (unlike commonly available double-balanced mixers). Since the RPU transmits an unmodulated carrier pulse level of +16.8 dBm during the reply interval, the reply transmission RF power level at the transponder is roughly +16.8 dBm−43 dB−10 dB=−36.2 dBm at 5820 MHz. The free space path loss for the reply from the earpiece transponder to the RPU is the same as for the interrogation, i.e., 43 dB. The resulting reply level received at the RPU is −36.2 dBm−43 dB=−79.2 dBm. The minimum detectable reply level at the RPU is determined by system thermal noise, expressed as P=kTBF, where P is the noise power in watts, k is Boltzmann's constant (1.38 E−23 joule/K), T is the system noise temperature (taken as room temperature, or 290 K), B is the reply signal bandwidth (taken as 30 E+6 Hz from FIG. 3) and F is the noise figure (see the discussion of noise fundamentals in "Phaselock Techniques" by F. M. Gardner, John Wiley & Sons, 1979, or the space communication chapter of "Reference Data for Radio Engineers" for details). Modern low-noise components available for 6 GHz operation, e.g. the HP ATF-36077 mentioned earlier, have noise figures approaching unity (F=1, or 0 dB). The resulting system noise is P=1.2 E−13 W, or −99 dBm, giving a 20 dB SNR for the reply. Note that the SNR for replies is chosen to be greater than that for interrogations, as any loss inserted in the link path will have a greater effect on replies than interrogations for the implementation described here. For example, if the path loss increases by 8 dB, the SNR for the interrogation link is reduced by 8 dB (from 12 dB to 4 dB) while the SNR for the reply link decreases by 16 dB (from 20 dB to 4 dB).

Mutual RF interference: In the implementation of the full-featured embodiment described here, a single interrogation/reply cycle takes place between the RPU and each earpiece once every 80 microseconds, on the average. Since each interrogation/reply cycle has a duration of 6150 nsec, as many as thirteen non-overlapping time slots are available for time-division multiplexing to prevent mutual RF interference between users located in close proximity. Since each binaural user needs two time slots (one for each earpiece), the system described here is more than adequate for six binaural users in close proximity. Interrogations from another user's RPU will not generally interfere with interrogations from a user's own RPU if the maximum pulse levels from the other user's RPU are at least 6 dB below all pulse levels from the user's own RPU. For example, if a user's own RPU produces PPM interrogation pulses at a level of −42 dBm at the user's earpiece transponder detector diode, then pulse levels of −48 dBm at the same detector diode caused by transmissions from another RPU some distance away will not generally prevent proper operation due to PPM sync detection errors nor cause PPM data errors. Thus, +16.8 dBm (48 mW) pulses from an RPU located more than 7.3 meters (24 feet) away, for which the free space path loss is 65 dB, will not generally interfere with a user's system as the resulting pulse levels measured at the detector diode are 16.8 dBm−65 dB=−48.2 dBm. It follows that similar units operating with more than 7.3 meter (24 feet) separation do not require mutual synchronization through the use of time-division multiplexing. Note that two similar units using time-division multiplexing and spaced more than 1.2 meters (4.3 feet) apart can share the same time slot with overlapping PPM and DPSK pulses, since the free space path loss is 50 dB at that separation and +1.3 dBm (1.35 mW)−50 dB=−48.7 dBm.

Figure 6:
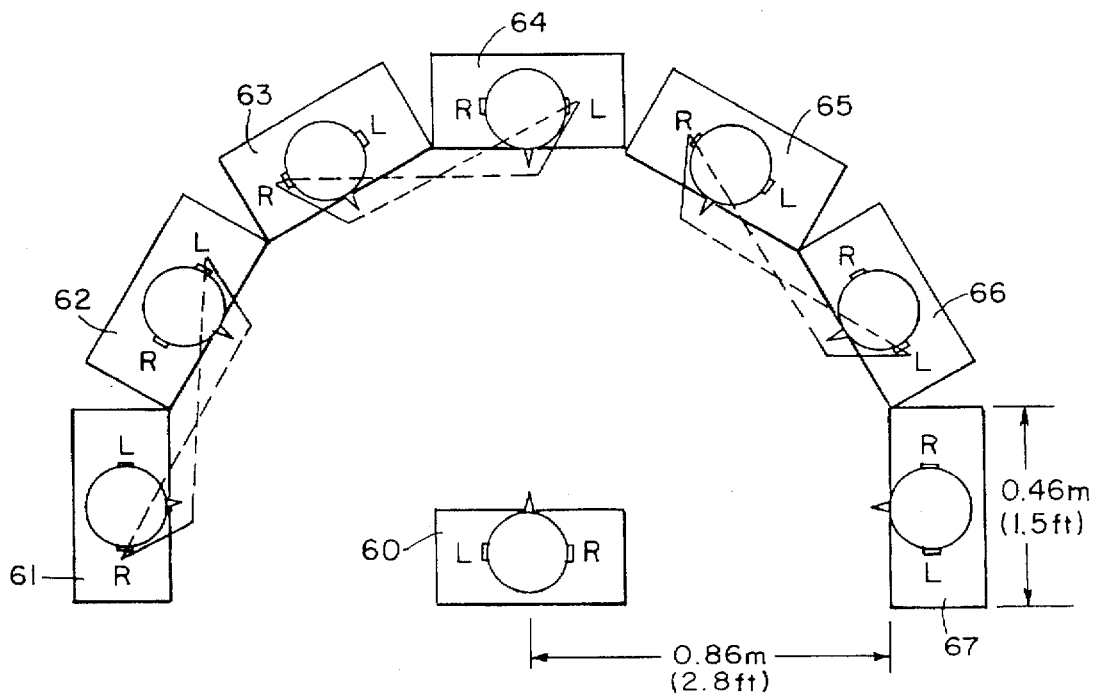
FIG. 6 is a bird's-eye view used to describe the RF mutual interference geometry occurring when many users of the invention are in close proximity.

Worst-case interference geometry: Crowds and auditorium seating do not represent a worst-case interference geometry due to body and seat shielding effects. Also, binaural users standing in a circle do not represent a worst-case interference geometry due to head shielding effects and increase of the circle diameter as more users are added. The worst known case, shown in the bird's-eye view of FIG. 6, occurs for a teacher 60 when seven students 61 through 67 stand in a shoulder-to-shoulder semicircle in front of the teacher. For analysis purposes, assume that the teacher and all students are binaural users with an RPU located near the navel. The teacher's pinnae (external ear cartilage) provide shielding from any students that may be standing behind the teacher. Seven students each having 0.46 meter (1.5 feet) shoulder width can stand 0.86 meter (2.8 feet) from the teacher. Adding more students increases their radial distance from the teacher and decreases mutual interference. Note that since eight binaural users are shown in FIG. 6, a total of sixteen time slots would be required were it not possible to share the thirteen available time slots provided by the system. Since many of the users are separated by more than 1.2 meters (4.3 feet), such users (e.g., students 61 and 67) could share the same time slot as described earlier, although such a possibility is not considered here. Many solutions (i.e., non-interfering time slot assignments) exist, with some requiring fewer than ten time slots for the geometry shown in FIG. 6. As a simple example, consider a solution in which only head shielding is used to provide the ability for multiple RPUs to share a single time slot, and all thirteen time slots are used. In FIG. 6, a solid line is used to represent a direct line-of-sight path between an earpiece and RPU, while a dashed line represents a non-interfering path with high loss due to head shielding. A user's left ear is denoted by the letter "L," while a user's right ear is denoted by the letter "R." FIG. 6 depicts a case where the teacher's 60 left (right) ear uses time slot #1 (#2), student 67's left (right) ear uses time slot #3 (#4), student 61's left ear uses time slot #5, student 62's right ear uses time slot #6, student 63's left ear uses time slot #7, student 64's right ear uses time slot #8, student 65's left ear uses time slot #9, student 66's right ear uses time slot #10, time slot #11 is shared by student 61's right ear and student 62's left ear, time slot #12 is shared by student 63's right ear and student 64's left ear, and time slot #13 is shared by student 65's right ear and student 66's left ear. Note that time slot numerical assignments are arbitrary. Since many solutions are possible, the time required for all units to reach an acceptable steady-state solution is minimal. As users move around, their hearing aid systems automatically adapt by continually finding new acceptable steady-state solutions using the time-domain multiplexing technique described earlier. This analysis indicates that a large number of users can operate similar devices in close proximity without disruptive mutual interference.

Figure 7:
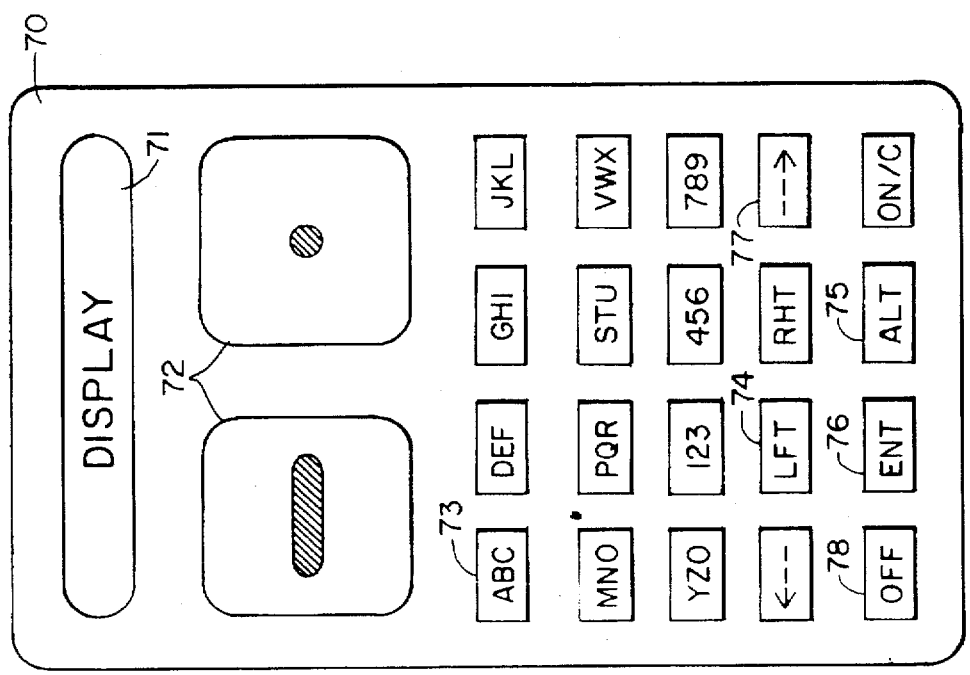
FIG. 7 is a drawing showing the front view of a typical RPU for a full-featured preferred embodiment of the invention.

RPU form factor: The remote processor unit can have a wide variety of form factors, a few of which are described here. The RPU can be worn as a wristwatch or other inconspicuous piece of jewelry, carried in a pocket or a purse, or worn on a belt over or under clothing. When manual command of RPU functions (e.g., control of parameter settings or data entry) is desired, a keyboard attached to or built into the RPU housing can be used. The keyboard may contain a full miniature alphanumeric keypad, or may consist of a few simple controls with very large pushbuttons for users with limited dexterity. If desired, the keyboard can be covertly operated while located, for example, in a user's pocket. One possible form factor of interest is shown in FIG. 7, where the RPU case 70 is a PCMCIA (Personal Computer Memory Card International) Type III PC Card with dimensions 54 mm (2.13 inches) wide, 85.6 mm (3.37 inches) long and 10.5 mm (0.41 inch) thick. The unit has an alphanumeric liquid crystal display 71, a pair of large pushbuttons 72 for rapid covert data entry via Morse code (or any other code for which a user performs data entry by applying pressure in a sequential pattern to one or more RPU keys) and a full miniature alphanumeric pushbutton keyboard. Morse code data entry rates range from five words per minute (novice) to fifty words per minute (expert), and the user only sends Morse code (which is generally easier than receiving). See "The ARRL Handbook for the Radio Amateur" for a description of Morse code, electronic keyers and automatic reception of Morse code using computers. To operate the alphanumeric keyboard, a user pushes the desired character key followed by the LFT or RHT key as required. For example, the letter "A" is entered by pushing the ABC key 73, causing the letter "B" to appear on the display 71, followed by the LFT key 74, which changes the letter "B" on the display to the letter "A." Twelve alternate characters (period, comma, etc.) are printed on the case 70, one above each character key (the alternate characters are not shown in FIG. 7). The alternate characters appear on the display when the corresponding character key is pressed and then the ALT key 75 is pressed. Note that no character requires more than two keystrokes to enter. The enter (ENT) key 76 is pressed when the displayed message is ready to be sent from the user to the RPU DSP, the left and right arrow (key 77 in FIG. 7) keys are used to edit messages, and the power-on and clear key (ON/C) and power-off (OFF, key 78 in FIG. 7) keys are used to control the RPU power. As shown in FIG. 9, a DSP 948 such as the Motorola DSP56L002 integrated circuit may supply the processor capabilities required for operation of the keyboard 946, display 954, Morse code keys 956 and other RPU features previously described and to be described later.

Location of misplaced system components: Modern CIC hearing aid earpieces 10 of the type possibly used in this invention may be smaller than the head of a cotton swab, and are easily misplaced (as are small RPUs 16). If the two-way wireless link between an earpiece and RPU 17 is interrupted for a certain period of time, as occurs when an RPU is misplaced, the earpiece automatically simulates stand-alone CIC hearing aid operation and the RPU, detecting a link disruption as described earlier, conserves power by reducing its number of attempts to communicate with the earpiece. If no interrogation is received by the earpiece 10 from the RPU 16 for a certain period of time (e.g., 0.1 second), as determined for example by a retriggerable monostable multivibrator circuit (also known in the art as a "one-shot") implemented in the earpiece ASIC 845, the ASIC initiates simulation of a stand-alone CIC hearing aid earpiece. Stand-alone operation is provided when the ASIC 845 causes signals from the microphone 875 via the 8-bit compressing A/D 880 to be routed to the speaker 855 via the 8-bit expanding D/A 850. In the simplest case, the ASIC 845 reads data from the A/D 880, performs a multiplication of the data by a constant (read from the default parameter storage 870) to provide amplification, compares the result with maximum allowable values (read from the default parameter storage 870) and writes the result to the D/A 850. The ASIC 845 may perform other processing (e.g., adaptive volume control) as well. Although none of the remote processor and communication features are available in stand-alone mode, which uses pre-selected hearing aid parameter settings from the default parameter storage 870 in the earpiece, the earpiece provides a useful amplified audio path from the microphone to the speaker. When communication between the earpiece and RPU resumes, a verbal message generated by the RPU DSP 948 (using, e.g., synthesized or pre-stored digitized speech) is sent to the earpiece to inform the user that system capabilities have been restored. Thus, to locate a misplaced RPU, a user simply wears an earpiece while moving around searching for the RPU. When a message from the RPU is heard in the earpiece, the RPU can be found nearby. Conversely, if an earpiece is misplaced, the user manually activates (using, for example, the keyboard 946) a search mode program (i.e., a DSP 948 program that indicates on the display 954 that communication has been established with an earpiece) in the RPU and observes the RPU display 954 while moving around searching for the earpiece. In systems with multiple earpieces, a different display 954 indication may be given for each earpiece.

Stand-alone earpiece operation: If an earpiece cannot communicate with an RPU for any reason, stand-alone earpiece operation as a CIC hearing aid is generally desirable. Examples include occasions where the RPU must be turned off by pushing the RPU power-off key 78 (e.g., situations where operation of wireless transmitters is prohibited such as aircraft takeoffs and classified military briefings), RPU battery or other RPU electronics failure, misplacement of an RPU, and primary wireless link 17 interference. Note that a microphone located in the earpiece 10 is preferred to a body-worn microphone, since only an earpiece microphone 12 can be used to provide the desired default CIC hearing aid function (earpiece microphones also provide superior audio localization capabilities as the microphone moves with the user's head, and provide reduced wind and clothing noise compared with body-worn microphones). Parameters that control the stand-alone earpiece operation are stored in the earpiece CIC default parameter storage 870, which is accessed by the ASIC 845 to implement the desired stand-alone functions as described earlier. CIC default parameters include, but are not limited to, settings for the nominal and maximum allowable earpiece volume. Other information contained in the default parameter storage 870 includes, but is not limited to, the communication address and L/R (left/right) selection bit. To ensure that the CIC default parameter storage information cannot be changed inadvertently, changes are only allowed when the earpiece is not in use as, for example, when the earpiece battery 860 is being charged. A battery charging detector 840, that is sensitive to the high-level magnetic induction fields commonly used for earpiece battery charging, indicates to the ASIC 845 that the default parameter storage 870 values may be changed upon receipt of an appropriate command from the RPU. Specifically, to change information in the earpiece CIC default parameter storage 870, a user first activates the earpiece battery charging system, e.g., by placing the earpiece in a recharger/storage tray well known in the art. The RPU keyboard 946 is then used to enter a command to the DSP 948 that indicates the user's desire to change information in the default parameter storage 870, followed by the new information to be stored. The DSP 948 causes the RPU to transmit an interrogation with a reserved address code to which all earpieces being charged within the communication range of the RPU are receptive. The information that is to ultimately be loaded into the earpiece default parameter storage 870 is then transmitted by the RPU using the auxiliary bit field of many successive interrogations, said interrogations are received by the earpiece, and the desired information is loaded into the CIC default parameter storage 870 under control of the ASIC 845.

Details of normal system operation: During normal operation of the hearing aid with wireless remote processor, sounds from the ambient environment are picked up by a microphone 12 in the earpiece 10 and transmitted with other information (e.g., data representing the earpiece battery 860 voltage as obtained by an A/D 865 converter and transmitted under control of the earpiece ASIC 845 in the auxiliary bit of many successive replies via the reply data register 825) over a primary two-way wireless link 17 to the RPU 16, where the audio signals are enhanced according to the user's needs by the RPU DSP 948. Signal enhancement is achieved via any of a number of techniques well known in the art that use the capabilities of the general-purpose RPU DSP 948. The enhanced audio signals may be combined with other information (e.g., a synthesized voice, generated within the DSP 948, warning that the aforementioned earpiece battery voltage is low) and transmitted from the RPU 16 over the primary wireless link 17 to the earpiece 10, where they are converted by a speaker 15 to sounds that can only be heard by the user 11. Art auxiliary speaker can be supplied in the RPU 16 as a peripheral 950 device that allows people other than the user to hear the same sounds as those produced by the earpiece speaker 15, if desired (as, e.g., when a person other than the user wishes to use the system's optional cellular telephone capabilities). A different, optional secondary two-way wireless link (shown as part of the RPU in FIG. 9 as secondary wireless link circuitry 944, or connected to the RPU by a wired or other, e.g. infrared, wireless link 18 and shown as optional secondary wireless link circuitry 19 in FIG. 1) can be used for communication between the RPU and a cellular telephone system or other sources of information. An RPU keyboard suitable for covert data entry 72, or voice recognition capabilities in the RPU (implemented, e.g., using any of a number of techniques well known in the art that use the general-purpose RPU DSP 948), can be used to control hearing aid parameters (such as amplification level set by the RPU DSP 948) and telephone dialing functions (e.g., automatic dialing of a predefined telephone number using information stored in the RPU DSP 948) in a manner that can be made imperceptible to a casual observer if desired.

Binaural, directional noise-canceling hearing aid with hearing protection: Two earpieces (one in each ear) and an RPU can be used in a binaural, directional noise-canceling hearing aid system with hearing protection features. Such a system provides some measure of protection for the residual hearing capability of a hearing-impaired user simultaneous with the hearing aid function. Note that the hearing protection provided by this invention is not presently certified as a replacement for OSHA (Occupational Safety and Health Administration) approved hearing protection devices required for high-noise environments. The hearing protection features of this invention are also available to users without hearing impairments and who wish to avoid a hearing impairment. In applications as aids for high risk of hearing loss groups such as firefighters, hunters and foot soldiers, the system may also provide hearing enhancement (e.g., amplification) for superior audio detection and direction-finding capabilities as well as hearing protection from loud equipment, shoulder-fired weapons or local artillery. The system is also capable of tinnitus masking and performing active noise cancellation to potentially enhance a user's mental concentration abilities using techniques well known in the art and implemented in the RPU DSP 948. The hearing protection function is achieved by limiting the amplitude of the audio signal produced by the earpiece (such limiting taking place in the earpiece under control of the ASIC 845), and also by having the earpiece create sound waves in opposition to sounds in the environment to effectively cancel loud sounds (using techniques well known in the art and implemented in the RPU DSP 948). Background noise and competing talker cancellation are achieved using any of a number of techniques and circuits well known in the art, e.g., variations of the Least Mean Squares (LMS) technique as implemented in the Motorola DSP56200 LMS filter integrated circuit, or the equivalent function implemented in the general-purpose RPU DSP 948. Note that for all binaural signal processing functions, data contained in replies from the left earpiece (i.e., audio data from the left earpiece microphone) is processed in the RPU DSP 948 by combining said data with other data contained in replies from the right earpiece (i.e., audio data from the right earpiece microphone). The processed audio data transmitted from the RPU to the left and right earpiece speakers via RPU interrogations is therefore a function of data received from both the left and right earpiece microphones via earpiece replies.

Unsolicited information: The invention provides useful unsolicited information (i.e., information automatically provided to the user by the system, not as a result of a user request for information) to the user of the system in a manner that can be made imperceptible to a casual observer if desired. Information about the status of the hearing aid system itself, such as a verbal warning that an earpiece or RPU battery voltage is low, is provided to the user as detailed earlier. Automatic measurements of heart pulse rate, body temperature and walking distance traveled can be taken by sensors 950 in the RPU 16 or earpiece 10 and stored in the RPU DSP 948. Sensor measurements can be reported to the user by a voice synthesized in the RPU DSP 948 using any of a variety of synthesis techniques well known in the art, including playback of pre-recorded digitized speech. The voice signal produced within the RPU DSP 948 is then added to the processed audio signals already being sent from the RPU to the earpiece. The RPU may also contain a local database of information in the DSP 948, including a time-of-day clock, which would allow a user to be alerted when it is time to take medication and be given verbal instructions on what to take. A sensor 950 attached to the RPU can continuously monitor the blood sugar level of diabetic users, enabling the system to provide verbal advice regarding insulin injections. The system can also remind a user to be in a certain location at a given time ("appointment reminders"), and provide current location information (based on inputs from sensors 950) as well as directions to individuals such as nursing home residents, using programs implemented in the RPU DSP 948.

Solicited information: Solicited information is provided by the system (e.g., via the earpiece speaker 15) in response to user requests (e.g., via an RPU keyboard 946, Morse code keys 956 or voice recognition capabilities implemented using the RPU DSP 948) in a manner that can be made imperceptible to a casual observer if desired. In this respect, the system acts as a "virtual handset" communication aid that replaces a conventional telephone handset in many applications (although users may additionally communicate with a conventional handset or speakerphone in the usual fashion). To accomplish the virtual handset function, the RPU 16 is equipped with optional secondary two-way wireless link circuitry 19 to communicate with a telephone or other communication network. The secondary wireless link is separate from, and does not interfere with, the primary wireless link 17 between the earpiece 10 and RPU 16. In applications where relatively high-power transmissions take place on the secondary link and the secondary link transmitter is integrated into the RPU, the RPU can be placed on a user's wrist or ankle away from vital organs to reduce any potential health risk relative to conventional wireless handsets. Note that transmissions on the primary link 17 between the earpiece and RPU use extremely low power levels which are not known to pose any health risk (see the Microwave Radiation Hazards section of "Reference Data for Radio Engineers" and ANSI/IEEE C95.1-1991 for specific recommendations). Alternatively, a separate cellular telephone transceiver not physically integrated with the RPU can be worn on the user's wrist or ankle and communicate with an RPU in the user's pocket (which in turn communicates with one or more earpieces) via a wired or wireless two-way link as shown, e.g., in link 18 of FIG. 1. It will be clear to those skilled in the art that any number of such links can be used to supplement the operation of this invention, and links using many different wireless transmission media (e.g., infrared or ultrasonic) and frequencies can be used, as can wired connections.

Obtaining solicited information: To obtain solicited information, user requests are processed in a variety of means well known in the art, including inputs via one or more pushbuttons on the RPU and voice recognition computer programs implemented in the RPU electronics. Voice recognition can be used almost exclusively, if desired, thereby eliminating nearly all RPU pushbutton controls. Voice commands recognized by the RPU can cause the RPU to initiate actions such as changing hearing aid parameter settings (e.g., volume), or activate appliances and environmental controls (e.g., aids for the physically handicapped) in a distributed wireless network via the secondary wireless link. RPU circuitry may also enable a user to voice-dial a desired telephone number by speaking certain pre-defined commands. The verbal commands are received as audio signals by the earpiece 10 and transmitted to the RPU 16. The RPU may contain a low-cost talker-dependent discrete-utterance limited-vocabulary voice recognizer capable of performing telephone dialing and other simple functions such as hearing aid parameter control. Such voice recognizers comprising a single integrated circuit are well known in the art, and can be attached to the DSP 948 as a peripheral 950. Alternatively, the voice recognition function can be performed by the DSP 948 itself. When the proper verbal command sequence is recognized, the RPU makes an appropriate connection to the telephone system via the secondary wireless link circuitry 944. A telephone connection may be made between the RPU and cellular, satellite, or other fixed or mobile resources. In emergency situations, the system may automatically dial an appropriate emergency service (based on information previously stored by the user in the RPU DSP 948), send voice or digital information regarding location, current medical situation (e.g. heart pulse rate) and medical history data (stored in the RPU DSP 948) in addition to providing normal telephone voice communication via the secondary wireless link circuitry 944.

Sensors and peripheral devices: Many sensors and peripheral devices 950 can reside in or be attached to the RPU by wired or wireless means, and controlled by the user (via inputs to the RPU DSP 948 through the keyboard 946, Morse code keys 956 or voice recognition) to provide both solicited and unsolicited information. Music can be provided from pre-stored information including tape, compact disc, over-the-telephone services via the secondary wireless link, or a commercial broadcast radio receiver. User location information can be provided to the RPU from special-purpose transmitters at specific locations in nursing home applications. Self-contained user-carried inertial navigation packages (with solid-state gyroscopes, accelerometers and a compass) or a Global Positioning System receiver can also be used. Sensors for a foot soldier RPU application may include many types of detectors such as RF detectors (e.g., radar detection capability), nuclear/biological/chemical weapon detectors, infrared or laser detectors and metal detectors. Appropriate verbal warnings or distinctive alerting tones generated by the RPU DSP 948 are sent from the RPU 16 to the earpiece 10 and ultimately received as audio signals by the user.

Secondary link applications: In foot soldier or firefighter applications, the secondary wireless link circuitry 19 may include the capability to directly access the RPU of other users, or communicate with radio "base stations" for local area networking with or without use of the general subscriber telephone system. Digital transceivers on the secondary links allow many units to operate in close proximity, and spread-spectrum techniques well known in the art can be used on all links (primary and secondary) if privacy, security, low probability of signal intercept and immunity from intentional interference (jamming) are required. Connection with a central human operator via the secondary link circuitry 19 may be desirable in situations requiring real-time language translation and emergency instructions, such as firefighting or multi-national force military operations. Note that in applications such as firefighting, it is not necessary to completely hide the hearing aid system and a visible RPU antenna is acceptable.

RPU computer applications: The combination of an earpiece 10 with an RPU 16 can be used in lieu of a laptop computer or "personal digital assistant" in many instances, and results in a practically theft-proof system. The system facilitates text-to-speech translation of electronic mail messages and faxes, where information is received via the secondary link and processed by the RPU DSP 948. Voice mail messages and paging services are readily accommodated by the system via the secondary wireless link 19 circuitry, with both digital data and speech signals exchanged between the RPU and a remote-site computer. The RPU DSP 948 can digitally generate tones so that a vocalist using the invention can produce a desired pitch without the need for an external reference such as a pitch pipe, and the secondary link capabilities can allow prompting for actors and public speakers. If connection to a remote-site computer is desired for database access, a highly capable large-vocabulary voice recognizer can be used at the remote site to process incoming audio signals over the secondary wireless link. Note that unlike the limited-capability RPU voice recognizer which may only recognize a few verbal commands, a remote-site voice recognizer accessed through a secondary link telephone connection need not be low-power nor portable, and can handle many users. The remote-site recognizer may also include talker voice identification capabilities (automated "voiceprint" analyses well known in the art) to prevent unauthorized use, and such capabilities may also be desirable in the RPU (and can be implemented, e.g., in the RPU DSP 948) for certain applications.

Secondary link audio considerations: In some applications, a user may not wish to transmit signals from the ambient audio environment over the secondary wireless link. In such cases, an auxiliary earpiece microphone which favors the "bone conduction" path over the normal "air path" between the user's mouth and ear can be used. To save space, the auxiliary microphone may be housed in the same miniature case as the primary earpiece microphone. Alternatively, when two earpieces are used, unwanted ambient sources can be "nulled out" in the RPU DSP 948 by digital signal processing techniques well known in the art (e.g., the equivalent of speakerphone circuitry). Note that such binaural signal processing techniques can also provide directivity and background noise cancellation for users having total hearing loss in one ear and partial loss in the other ear, as discussed earlier in connection with binaural hearing aid system operation.

Hearing test: The present invention allows hearing tests to be performed via the earpiece normally worn by the user, without the need for additional expensive test equipment. All signal generation capabilities necessary to perform hearing tests are available in the hearing aid system comprising an earpiece 10 and RPU 16. Specifically, the RPU DSP 948 can be used to generate tones of varying frequencies and amplitudes, as well as other signals known to be useful for hearing test purposes (e.g., nonsense syllables) that are converted to acoustic waves by the earpiece. Such tones are used to perform a hearing test that determines appropriate gain vs. frequency parameters for a program stored in the RPU DSP 948 that performs signal enhancement to compensate for the user's hearing loss. Note that the hearing test program that controls the RPU DSP 948 during the hearing test can be temporarily stored in the RPU DSP 948 for the duration of the test, then deleted upon completion of the test to allow re-use of RPU DSP 948 memory resources during normal operation. The hearing test program may be loaded into the RPU DSP 948 through the secondary wireless link 944 or a wired peripheral link 950.

Figure 10:
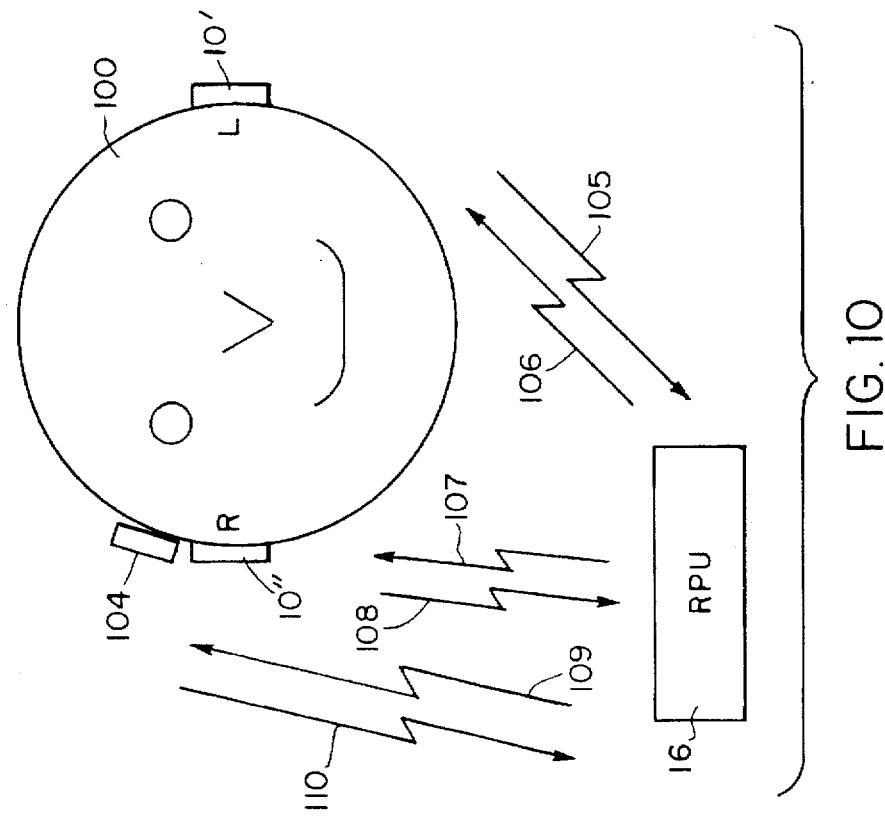
FIG. 10 is a block diagram showing details of a wireless cochlear implant system.
Figure 11:
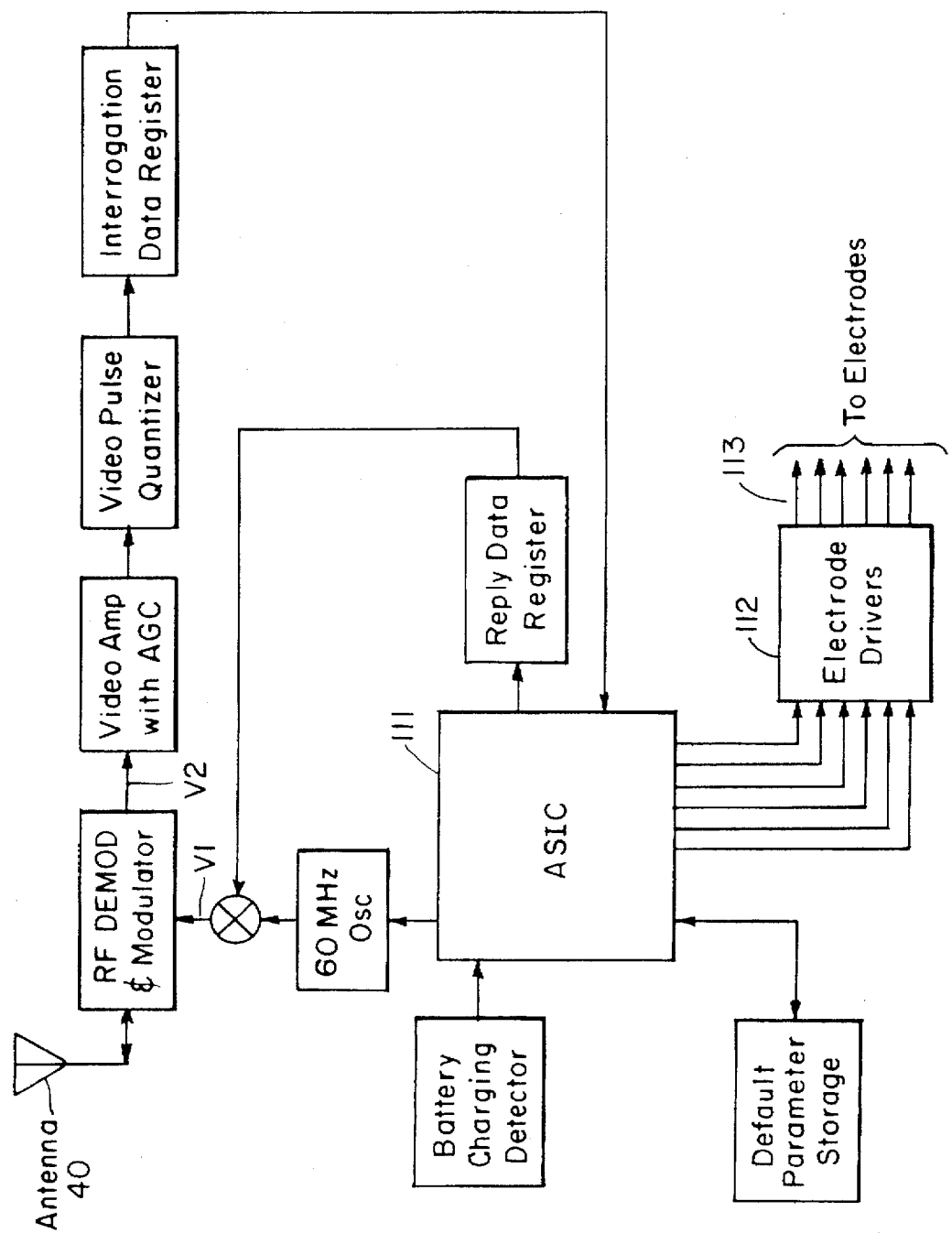
FIG. 11 is a block diagram showing details of a wireless cochlear implant electrode driver unit.

Cochlear implants: Features previously described for the full-featured preferred embodiment of the hearing aid with wireless remote processor including, if desired, communication via a secondary link, can also be implemented in a wireless cochlear implant system as shown in FIG. 10. Profoundly deaf cochlear implant patients can be provided with a wireless system having improved performance, appearance and freedom of movement compared to existing wire-connected systems. Cochlear implants are almost always monaural devices, i.e., only one ear is used for an implant in a particular patient. Because of this, patients often have trouble understanding a talker in the presence of other talkers or background noise (the "cocktail party effect" well known in the art). Patients also have difficulty adjusting to the voices of different talkers, making conversation difficult even in the absence of competing talkers and background noise. To combat these problems, a user 100 is equipped with a pair of CIC wireless hearing aid earpieces (left 10' and right 10"), an RPU 16 and wireless BTE implant electrode driver unit 104 (which is not necessarily imperceptible to a casual observer). Note that a system using only one earpiece is also possible, but a more generally applicable system that uses two earpieces is described here. The driver unit 104 contains transceiver circuitry similar to that used in an earpiece 10 transponder (see FIG. 11), with differences as noted in the following, and electrode driver circuitry 112 well known in the prior art for driving the cochlear implant electrodes 113. Speakers 15 in the left and right earpieces serve no purpose in the cochlear implant application, as the user is profoundly deaf, and may be disconnected to conserve power. An interrogation RF signal travels on a path 106 from the RPU 16 to the left earpiece 10', and the same interrogation RF signal travels via another path 109 from the RPU to the driver unit 104. The left earpiece 10' is responsive to a specific address bit pattern contained in the interrogation, as explained earlier, and the driver unit 104 is also responsive to the same address. Audio and auxiliary data bits in the interrogation are received simultaneously by both the left earpiece 10' and driver unit 104. The left earpiece 10' uses the received interrogation data bits to compute a parity bit for the subsequent reply, while the driver unit 104 uses the interrogation audio data bits to drive the cochlear implant electrodes and the auxiliary bit for synchronization, as described later. The left earpiece 10' transmits a reply in response to a properly addressed interrogation, if said interrogation has an L/R (left/right) bit value of logic "1," that travels via path 105 to the RPU 16 and contains ambient audio and other (auxiliary bit and parity bit) data, but the driver unit 104 does not reply. The driver unit 104 circuitry is slightly different from earpiece transponder circuitry in that the driver unit 104 never replies via path 110 except in response to interrogations that have a special reserved address used during the process of locating a misplaced driver unit 104 with an RPU 16. This and other features of the driver unit 104 can be implemented, e.g., through use of an ASIC 111, similar to the earpiece ASIC 845, that controls reply transmissions as well as other functions (e.g., data synchronization as described later) of the driver unit. The procedure for locating a misplaced driver unit 104 using an RPU 16 is the same as that described earlier for locating a misplaced earpiece using an RPU (except the user activates an RPU search mode program that uses the special reserved address for locating cochlear implant driver units), and the procedure for locating a misplaced RPU 16 using a driver unit 104 is the same as that described earlier for locating a misplaced RPU 16 using an earpiece 10. Similarly, an interrogation RF signal travels on a path 107 from the RPU 16 to the right earpiece 10", and the same interrogation RF signal travels via another path 109 from the RPU to the driver unit 104. The right earpiece 10" is responsive to a specific address bit pattern contained in the interrogation (the same address as the left earpiece 10'), and the driver unit 104 is also responsive to the same address. Audio and auxiliary data bits in the interrogation are received simultaneously by both the right earpiece 10" and driver unit 104. The right earpiece 10" uses the received data bits to compute a parity bit for the subsequent reply, while the driver unit 104 uses the audio data bits to drive the cochlear implant electrodes and the auxiliary bit for synchronization, as described later. The right earpiece 10" transmits a reply in response to a properly addressed interrogation with the L/R bit set to a logic "0," that travels via path 108 to the RPU 16 and contains audio and other (auxiliary bit and parity bit) data, but the driver unit 104 does not reply. Audio signals from the earpiece microphones are converted in the RPU 16 by the DSP 948 to a single audio output signal with superior signal-to-noise ratio. Background noise and competing talker cancellation are achieved using any of a number of techniques or circuits well known in the art, e.g., variations of the Least Mean Squares (LMS) technique as implemented in the Motorola DSP56200 integrated circuit, or the equivalent function implemented in a program executed by the RPU DSP 948. The noise-canceled signal is then further processed by, e.g., a normalization program implemented in the RPU DSP 948 that reduces talker variability with regard to volume level, average pitch, pitch range and tone. The resulting noise-canceled and normalized signal is then processed, e.g., by a program implemented in the RPU DSP 948 to create appropriate signals that will subsequently drive the individual electrodes of a cochlear implant via the implant driver 104. The number of electrode driver signals depends upon the type of implant as well as the number of functional electrodes in a given patient. The appropriate signals are transmitted in the audio data field of RPU interrogations from the RPU 16 to the implant driver 104 via path 109. The implant driver 104 then receives data in the interrogation audio data field and converts the data in the ASIC 111 to signals supplied to the electrode drivers 112 used to stimulate the cochlear implant electrodes 113 by means well known in the prior art. The average audio data rate from the RPU 16 to the implant driver 104 is 200 Kbits/sec. The data rate for cochlear implants in the prior art is typically 144 Kbits/sec (12 bits/sample at a rate of 2000 samples/sec to each of 6 electrodes), and this rate is easily supported by the system described here. In the wireless cochlear implant system, the 200 Kbits/sec data stream from the RPU 16 to the implant driver 104 is controlled, e.g., by interrogation auxiliary link messages that provide information used by the implant driver 104 ASIC 111 to separate the received serial data stream into data presented, e.g., in a parallel form suitable for the electrode drivers 112 to use in driving the individual electrodes 113. The wireless cochlear implant system is compatible with the wireless hearing aid system described earlier, and the wireless cochlear implant system occupies the same number of interrogation/reply time slots as a wireless binaural hearing aid system.

This completes the description of the preferred and alternate embodiments of the invention. Those skilled in the art may recognize other equivalents to the specific embodiments described herein which equivalents are intended to be encompassed by the claims attached hereto.

What is claimed is:

1. A hearing aid system comprising an earpiece suitable for being worn at the head of a user, and a processor unit, said earpiece comprising, a microphone responsive to a first sound from the environment, present at the input of said microphone, to provide a first electrical signal, a first wireless reflective transponder to provide a first wireless transmission in response to said first electrical signal by modulating energy from a wireless interrogator, a first wireless receiver to receive a second wireless transmission to generate a second electrical signal, said second electrical signal being an enhanced version of said first electrical signal, a speaker transducer responsive to said second electrical signal to convert said second electrical signal into a second sound;

said processor unit comprising, a second wireless receiver responsive to said first wireless transmission to provide a third electrical signal that is a replica of said first electrical signal, a signal processor responsive to said third electrical signal to provide a fourth electrical signal, said fourth electrical signal being an enhanced version of said third electrical signal, said wireless interrogator being responsive to said fourth electrical signal to provide said second wireless transmission of said fourth electrical signal, said second electrical signal being a replica of said fourth electrical signal.

2. The hearing aid system of claim 1 wherein
said earpiece and said processor are remote from each other by being separated by a distance no greater than the maximum usable communication range.

3. The hearing aid system of claim 1 wherein
said earpiece comprises a left and right earpiece, each left and right said earpiece producing a left and right said third signal, respectively,
said signal processor being responsive to left and right said third signals to provide left and right said fourth signals, respectively,
left and right said earpieces being responsive to left and right said fourth signals, respectively.

4. A hearing aid system comprising,
means for converting acoustic waves into electrical signals, and for converting said electrical signals into acoustic waves, said converting means further including a reflective transponder for transmitting said electrical signals via a first wireless communications link by modulating energy from an interrogator; and
means for processing said electrical signals received via said first wireless communications link into enhanced audio signals, said processing means further including said interrogator for transmitting said enhanced audio signals back to said converting means via said first wireless communications link, said processing means further including a second communications link with a source other than said converting means.

5. Hearing aid system according to claim 4, wherein said processing means produces said enhanced audio signals according to a hearing impairment of a user.

6. Hearing aid system according to claim 4, wherein said converting means includes a microphone for converting said acoustic waves into said electrical signals, a speaker for converting said electrical signals into acoustic waves, and wherein said transponder is a wireless transceiver.

7. Hearing aid system according to claim 6, wherein said converting means is configured for insertion into a human ear canal.

8. Hearing aid system according to claim 6, wherein said converting means is configured as a cochlear implant.

9. Hearing aid system according to claim 4, wherein said second communications link is a unidirectional link for providing text to speech translation.

10. Hearing aid system according to claim 4, wherein said second communications link is a bidirectional link for interfacing with an external communications network.

11. Hearing aid system according to claim 4, wherein said second communications link is a wireless link.

12. Hearing aid system according to claim 4, wherein said second communications link is a wired link.

13. Hearing aid system according to claim 4, wherein said processing means is programmed by voice commands transmitted to the processing means via said first wireless communications link.

14. Hearing aid system according to claim 4, wherein said processing means further includes,
means for keyed entry of coded data.

15. Hearing aid system according to claim 14, wherein said coded data is Morse code data.

16. Hearing aid system according to claim 4, wherein said processing means further includes,
means for generating at least one of an acoustic locator tone and a visual locator display.

17. Hearing aid system according to claim 4, wherein said convening means further includes,
means for generating an acoustic locator tone.

18. Hearing aid system according to claim 4, wherein said converting means further includes,
at least one of a radio frequency antenna and an infrared fiber optic cable configured as a simulated strand of hair which also serves as a means for extracting said converting means from an ear canal.

19. Hearing aid system according to claim 4, wherein said first wireless communications link operates at a frequency of at least 5 GHz.

20. Hearing aid system according to claim 4, wherein said converting means is a monaural earpiece.

21. Hearing aid system according to claim 4, wherein said converting means includes binaural earpieces.

22. Hearing aid system according to claim 4, wherein at least one of said converting means and said processing means further includes, plural antennae to accommodate transmission path losses within said wireless communications link.

23. Hearing aid system according to claim 4, further comprising, means for automatically placing said converting means into a self-contained hearing aid default mode upon loss of said first wireless communications link with said processing means.

24. Hearing aid system according to claim 4, wherein said first wireless communications link is a radio frequency link.

25. Hearing aid system according to claim 4, wherein said first wireless communications link is an infrared link.

26. Hearing aid system according to claim 4, wherein said first wireless communications link is an ultrasonic link.

27. Hearing aid system according to claim 4, wherein said first wireless communications link is a microwave link.

28. Hearing aid system according to claim 4, wherein said processing means further includes, means for performing an in situ hearing test to program said processing means for processing said electrical signals into said enhanced audio signals.

29. Hearing aid system according to claim 4, wherein said processing means further provides binaural directional noise cancellation.

30. Hearing aid system according to claim 4, wherein said electrical signals are coded with an address of said converting means.

31. Hearing aid system according to claim 4, wherein said converting means outputs said acoustic waves via a bone conduction path.

32. Hearing aid system according to claim 4, wherein said processing means further includes, an additional means for converting electrical signals into acoustic waves.

33. A hearing aid system earpiece comprising, a microphone for converting acoustic waves into electrical signals;

a speaker for converting said electrical signals into acoustic waves subsequent to remote enhancement of said electrical signals; and a reflective transponder for transmitting said electrical signals via a first communications link by modulating energy from an interrogator.

34. Hearing aid system earpiece according to claim 33, wherein said first communications link is a wireless bidirectional communications link.

35. Hearing aid system earpiece according to claim 33, wherein said transponder comprises at least one of a microwave transmitter and an infrared transmitter.

36. A hearing aid system signal processor comprising, means for processing acoustic signals received as electrical signals from a remote earpiece reflective transponder via a first wireless communications link into enhanced audio signals, and for transmitting said enhanced audio signals via said first wireless communications link to said remote earpiece; and a second communications link for simultaneous communicating with a source other than said remote earpiece.

37. A hearing aid according to claim 36, wherein said second communications link is a wireless link.

38. A hearing aid according to claim 36, wherein said second communications link is a wired link.

39. Apparatus for wireless communication comprising, means for converting acoustic waves into electrical signals, and for converting said electrical signals into acoustic waves, said converting means further including a reflective transponder for transmitting said electrical signals via a first communications link by modulating energy from an interrogator; and means for processing said electrical signals received via said first wireless communications link into processed signals, said processing means further including said interrogator for transmitting said processed signals back to said converting means via said first wireless communications link.

40. Apparatus according to claim 39, wherein said processing means further comprises, a second communications link for communicating with a source other than said converting means.

41. Apparatus according to claim 39, wherein said converting means is configured as an earpiece of a hearing aid system.

42. Apparatus according to claim 39, wherein said converting means is configured as a cochlear implant system.

43. Apparatus according to claim 39, wherein said converting means includes a microphone for converting said acoustic waves into said electrical signals, a speaker for converting said electrical signals into acoustic waves, and wherein said transponder is a wireless transceiver.

44. Apparatus according to claim 40, wherein said second communications link is a wireless link.

45. Apparatus according to claim 39, wherein said processing means is programmed by voice commands transmitted to the processing means via said first wireless communications link.

46. Apparatus according to claim 39, wherein said processing means further includes, means for keyed entry of coded data.

47. Apparatus according to claim 39, wherein said processing means further includes, means for generating at least one of an acoustic locator tone and a visual locator display.

48. Apparatus according to claim 39, wherein said converting means further includes, means for generating an acoustic locator tone.

49. Apparatus according to claim 39, wherein said converting means further includes, at least one of a radio frequency antenna and an infrared fiber optic cable configured as a simulated strand of hair which also serves as a means for extracting said converting means from an ear canal.

50. Apparatus according to claim 39, wherein said converting means includes binaural earpieces.

51. Apparatus according to claim 39, wherein at least one of said converting means and said processing means further includes, plural antennae to accommodate transmission path losses within said wireless communications link.

52. Apparatus according to claim 39, further comprising, means for automatically placing said converting means into a self-contained hearing aid default mode upon loss of said first wireless communications link with said processing means.

53. Apparatus according to claim 39, wherein said first wireless communications link is a radio frequency link.

54. Apparatus according to claim 39, wherein said first wireless communications link is an infrared link.

55. Apparatus according to claim 39, wherein said first wireless communications link is a microwave link.

56. Apparatus according to claim 39, wherein said processing means further includes, means for performing an in situ hearing test to program said processing means for processing said electrical signals into enhanced audio signals.

57. Apparatus according to claim 39, wherein said processing means further provides binaural directional noise cancellation.

58. Apparatus according to claim 39, wherein said electrical signals are coded with an address of said converting means.

59. Apparatus according to claim 39, wherein said converting means outputs said acoustic waves via a bone conduction path.

60. Apparatus according to claim 39, wherein said processing means further includes, an additional means for converting electrical signals into acoustic waves.

61. Apparatus for wireless communication comprising, means for converting acoustic waves into electrical signals, and for converting said electrical signals into acoustic waves, said converting means further including means for transmitting said electrical signals via a first wireless communications link; and means for processing said electrical signals received via said first wireless communications link into processed signals, and for transmitting said processed signals back to said converting means via said first wireless communications link, said processing means supplying operating power to said converting means via said first wireless communications link.

62. Apparatus according to claim 61, wherein said processing means further comprises, a second communications link for communicating with a source other than said converting means.

63. Apparatus according to claim 61, wherein said converting means is an earpiece of a hearing aid system.

64. Apparatus according to claim 61, wherein said converting means is a cochlear implant system.

65. Apparatus for wireless communication comprising, means for converting acoustic waves into electrical signals, and for converting said electrical signals into acoustic waves, said converting means further including reflective transponder means for transmitting said electrical signals via a first wireless communications link; and means for processing said electrical signals received via said first wireless communications link into processed signals, and for transmitting said processed signals back to said converting means via said first wireless communications link, said processing means further including a second communications link for simultaneous communicating with a source other than said converting means.

66. Apparatus for wireless communication comprising, means for converting acoustic waves into electrical signals, and for converting said electrical signals into acoustic waves, said converting means further including reflective transponder means for transmitting said electrical signals via a first wireless communications link;

means for processing said electrical signals received via said first wireless communications link into processed signals, and for transmitting said processed signals back to said converting means via said first wireless communications link; and means for receiving an audio command for voice activated programming said processing means via said first wireless communications link.

67. A method of improving audio communication with hearing impaired individuals comprising the steps of, illuminating an area in a vicinity of an ear of a hearing impaired person with a preselected carrier signal from a remote source, modulating said preselected carrier signal with environmental sound present in said vicinity to produce a modulated carrier, transponding said modulated carrier back to said remote source of said preselected carrier signal, and processing said modulated carrier to produce an enhanced audio signal for transmission to a transducer located in said vicinity.

68. A method of improving audio communication with hearing impaired individuals according to claim 67 wherein said step of modulating further includes a step of, establishing a separately modulated channel for each ear of said hearing impaired person.

69. A method of improving audio communication with hearing impaired individuals according to claim 67 wherein said preselected carrier signal is selected from a frequency range of between 300 megahertz and 300 gigahertz.

70. A method of improving audio communication with hearing impaired individuals according to claim 67 wherein said preselected carrier signal is an infrared signal.

71. A method of improving audio communication with hearing impaired individuals according to claim 67 which further includes the step of, receiving an audio transmission signal at said remote source, said audio transmission signal being received from another source and being processed with said enhanced audio signal for transmission to said transducer at said ear.

* * * * *